United States Patent
Foucart et al.

(10) Patent No.: US 12,053,456 B2
(45) Date of Patent: *Aug. 6, 2024

(54) PHARMACEUTICAL COMPOSITIONS FOR COMBINATION THERAPY

(71) Applicant: GENFIT, Loos (FR)

(72) Inventors: Corinne Foucart, La Madeleine (FR); Robert Walczak, Lille (FR); Carole Belanger, Bondues (FR); Benoît Noel, Gondecourt (FR)

(73) Assignee: GENFIT, Loos (FR)

( * ) Notice: Subject to any disclaimer, the term of this patent is extended or adjusted under 35 U.S.C. 154(b) by 406 days.

This patent is subject to a terminal disclaimer.

(21) Appl. No.: 17/316,115

(22) Filed: May 10, 2021

(65) Prior Publication Data

US 2021/0275504 A1    Sep. 9, 2021

Related U.S. Application Data

(63) Continuation of application No. 16/479,382, filed as application No. PCT/EP2018/052159 on Jan. 29, 2018, now Pat. No. 11,033,534.

(30) Foreign Application Priority Data

Jan. 27, 2017  (EP) ..................................... 17305094
Mar. 13, 2017  (EP) ..................................... 17305268
Sep. 12, 2017  (EP) ..................................... 17190723

(51) Int. Cl.
| | | |
|---|---|---|
| *A61K 31/426* | (2006.01) | |
| *A61K 31/192* | (2006.01) | |
| *A61K 31/40* | (2006.01) | |
| *A61K 31/428* | (2006.01) | |

(52) U.S. Cl.
CPC .......... *A61K 31/426* (2013.01); *A61K 31/192* (2013.01); *A61K 31/40* (2013.01); *A61K 31/428* (2013.01)

(58) Field of Classification Search
CPC .... A61K 31/426; A61K 31/192; A61K 31/40; A61K 31/428
See application file for complete search history.

(56) References Cited

PUBLICATIONS

Temann et al. The Journal of Experimental Medicine• vol. 188, No. 7, Oct. 5, 1998 1307-1320 (Year: 1998).*
Stankov The Open Inflammation Journal, 2012, 5, 1-9 (Year: 2012).*

* cited by examiner

*Primary Examiner* — Jeffrey S Lundgren
*Assistant Examiner* — William Y Lee
(74) *Attorney, Agent, or Firm* — Leason Ellis LLP

(57) ABSTRACT

The present invention relates to a combination product and its use in therapy.

Figure 1:
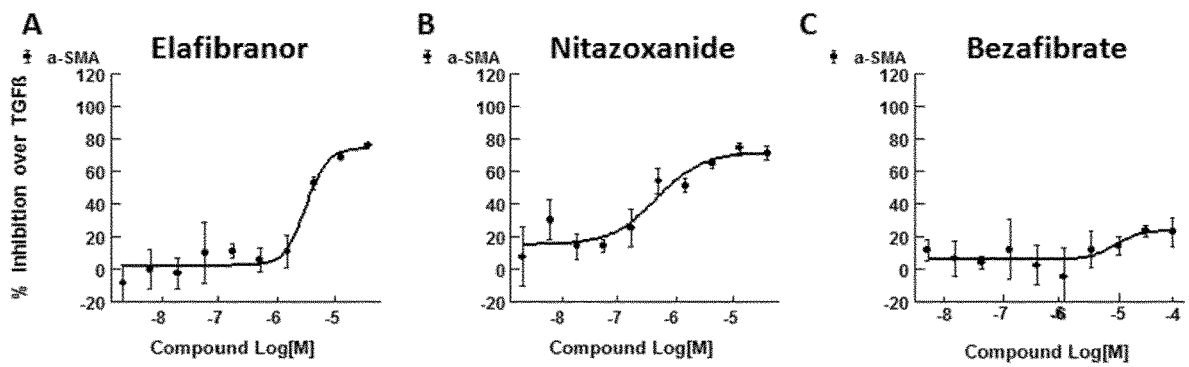

9 Claims, 11 Drawing Sheets
Specification includes a Sequence Listing.

Hepatic collagen

Histology

Hepatic aSMA gene expression

Hepatic CCR2 gene expression

Hepatic CCR5 gene expression

Hepatic MMP2 gene expression

Hepatic TIMP2 gene expression

Hepatic TGFb1 gene expression

PHARMACEUTICAL COMPOSITIONS FOR COMBINATION THERAPY

CROSS REFERENCE TO RELATED APPLICATION

The present application is a continuation application of U.S. patent application Ser. No. 16/479,382, filed on Jul. 19, 2019, now U.S. Pat. No. 11,033,534, which is a 371 US National Stage application of International Application No. PCT/EP2018/052159, filed on Jan. 29, 2018, which claims priority to European Patent Application Nos. EP 17305094.9 (filed on Jan. 27, 2017), EP 17305268.9 (filed on Mar. 13, 2017), and EP 17190723.1 (filed on Sep. 12, 2017), each of which is hereby incorporated by reference in its entirety.

The present invention relates to combinations of nitazoxanide (NTZ) or a derivative thereof in combination with a PPAR agonist for therapy.

[2-[(5-nitro-1,3-thiazol-2-yl)carbamoyl]phenyl]ethanoate, (or nitazoxanide, or NTZ), first described in 1975 (Rossignol and Cavier, 1975), was shown to be highly effective against anaerobic protozoa, helminths, and a wide spectrum of microbes including both anaerobic and aerobic bacteria (Rossignol and Maisonneuve, 1984; Dubreuil, Houcke et al., 1996; Megraudd, Occhialini et al., 1998; Fox and Saravolatz, 2005; Pankuch and Appelbaum, 2006; Finegold, Molitoris et al., 2009). It was first studied in humans for the treatment of intestinal cestodes (Rossignol and Maisonneuve, 1984) and it is now licensed in the United States (Alinia®, Romark laboratories) for the treatment of diarrhea caused by the protozoan parasites *Crystosporidium parvum* and Giardia intestinalis. NTZ has also been widely commercialized in Latin America and in India where it is indicated for treating a broad spectrum of intestinal parasitic infections (Hemphill, Mueller et al., 2006). The proposed mechanism of action by which NTZ exerts its antiparasitic activity is through the inhibition of pyruvate:ferredoxin oxidoreductase (PFOR) enzyme-dependent electron transfer reactions that are essential for anaerobic metabolism. (Hoffman, Sisson et al., 2007). NTZ also exhibited activity against *Mycobacterium tuberculosis*, which does not possess a homolog of PFOR, thus suggesting an alternative mechanism of action. Indeed, the authors showed that NTZ can also act as an uncoupler disrupting membrane potential and intra-organism pH homeostasis. (de Carvalho, Darby et al., 2011).

The pharmacological effects of NTZ are not restricted to its antiparasitic or antibacterial activities and in recent years, several studies revealed that NTZ can also confer antiviral activity (Di Santo and Ehrisman, 2014; Rossignol, 2014). NTZ interferes with the viral replication by diverse ways including a blockade in the maturation of hemagglutinin (influenza) or VP7 (rotavirus) proteins, or the activation of the protein PKR involved in the innate immune response (for a review, see (Rossignol, 2014)). NTZ was also shown to have broad anticancer properties by interfering with crucial metabolic and prodeath signaling pathways (Di Santo and Ehrisman, 2014).

The PPARs (α, β/δ (herein after δ), and γ), belong to the hormone-activated nuclear receptor family. The PPARs, or "Peroxisome Proliferator Activated Receptors", are nuclear receptors from the superfamily of transcription factors activated by the following ligands: steroids/thyroid hormones/retinoids. To date, three PPAR isotypes have been identified in mice and humans: PPARα, PPARδ and PPARγ. While PPARβ/δ expression in humans appears to be ubiquitous, PPARα and γ exhibit a differential tissue distribution (Braissant O and Wahli W, 1998). PPARα is expressed in cells with high fatty acid catabolic activity and in cells with high peroxisomal activity (hepatocytes, cardiomyocytes, renal proximal tubules, intestinal mucosa). PPARβ/δ is expressed ubiquitously and abundantly in most tissues. As far as PPARγ expression is concerned, it is limited mainly to adipose tissue, certain immune system cells and retina and is present in only trace amounts in other organs (Braissant O and Wahli W, 1998).

Taking the example of PPARα, its action is mediated by a class of compounds such as the fibrates which have a lipid-lowering effect. Natural ligands have also been identified such as for example fatty acids, eicosanoids (leukotriene B4) and 8(S)-hydroxyeicosatetraenoic acid (Kliewer S A et al., 1997). The PPARs have been associated primarily with lipid and glucose metabolism. PPAR activators, such as fibrates, enable a regulation of plasma cholesterol and triglyceride concentrations via activation of PPARα (Hourton D et al., 2001). Fibrate therapy leads to an increase in fatty acid oxidation in liver. Fibrates also decrease the synthesis of triglycerides (Staels B and Auwerx J, 1998). PPARα activators are also capable of correcting hyperglycemia and insulin level. Fibrates also reduce adipose tissue mass through a mechanism which is independent of food intake and leptin gene expression (Guerre-Millo M et al., 2000). The therapeutic interest of PPARγ agonists has been widely investigated in the treatment of type 2 diabetes (Spiegelman B M, 1998). It has been shown that PPARγ agonists restore insulin sensitivity in target tissues and reduce plasma glucose, lipid and insulin levels both in animal models of type 2 diabetes and in humans (Ram V J, 2003). PPAR activation by ligands also plays a role in regulating the expression of genes that participate in processes such as inflammation, angiogenesis, cell proliferation and differentiation, apoptosis and the activities of iNOS, MMPase and TIMPs. Activation of PPARαa in keratinocytes results in a cessation of their proliferation and expression of genes involved in differentiation (Komuves L G et al., 2000). The PPARs have anti-inflammatory properties because they negatively interfere with transcription mechanisms involving other transcription factors like NF-κB or transcriptional activators like STAT and AP-1 (Desvergne B and Wahli W, 1999). Said anti-inflammatory and anti-proliferative properties make the PPARs (and particularly PPARα) interesting therapeutic targets for the treatment of diseases such as vascular occlusive diseases (atherosclerosis, etc.), hypertension, diseases related to neovascularization (diabetic retinopathy, etc.), inflammatory diseases (inflammatory bowel disease, psoriasis, etc.) and neoplastic diseases (carcinogenesis, etc.)

The present invention describes novel combinations of NTZ analogues, and PPAR agonists and their use in therapy, in particular in the treatment of inflammatory, metabolic, fibrotic and cholestatic diseases.

The inventors found that NTZ, a synthetic antiprotozoal agent or its derivatives or its metabolites in combination with PPAR agonists show therapeutic activities that are useful in therapy, in particular for the treatment of immune, inflammatory, metabolic, fibrotic or cholestatic diseases.

Therefore, the present invention relates to a combination product comprising:
  (i) a compound selected from NTZ and an analogue thereof; and
  (ii) at least one PPAR agonist.

In a particular embodiment, the compound of component (i) of the combination product is a compound of formula (I):

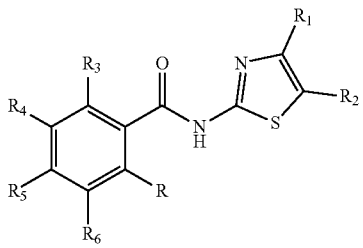

or a pharmaceutical acceptable salt thereof, in which

R1 represents a hydrogen atom (H), a deuterium atom (D), a halogen atom, a (C6-C14)aryl group, a heterocyclic group, a (C3-C14)cycloalkyl group, a (C1-C6) alkyl group, a sulfonyl group, a sulfoxyde group, a (C1-C6)alkylcarbonyl group, a (C1-C6)alkyloxy, a carboxylic group, a carboxylate group, a nitro group (N02), an amino group (NH2), a (C1-C6)alkylamino group, an amido group, a (C1-C6)alkylamido group, a (C1-C6)dialkylamido group.

R2 represents a hydrogen atom, a deuterium atom, a N02 group, a (C6-C14)aryl group, a heterocyclic group, a halogen atom, a (C1-C6)alkyl group, a (C3-C14)cycloalkyl group, a (C2-C6)alkynyl group, a (C1-C6) alkyloxy group, a (C1-C6)alkylthio group, a (C1-C6) alkylcarbonyl group, a (C1-C6)alkylcarbonylamino group, a (C6-C14)arylcarbonylamino group, a carboxylic or carboxylate group, an amido group, a (C1-C6) alkylamido group, a (C1-C6)dialkylamido group, a $NH_2$ group, a (C1-C6)alkylamino group, or R1 and R2, together with the carbon atoms to which they are attached, form a substituted or unsubstituted 5- to 8-membered cycloalkyl, heterocyclic or aryl group, R3, R4, R5, R6, and R7, identical or different, represent a hydrogen atom, a deuterium atom, a halogen atom, a hydroxyl group, a (C1-C6)alkylcarbonyl group, an (C1-C6)alkyl group, an (C1-C6)alkyloxy group, an (C1-C6)alkylthio group, an (C1-C6)alkylcarbonyloxy group, an (C6-C14)aryloxy group, a (C6-C14)aryl group, a heterocyclic group, a (C3-C14)cycloalkyl group, a N02 group, a sulfonylaminoalkyle group, an NH2 group, an amino(C1-C6)alkyl group, an (C1-C6) alkylcarbonylamino group, a carboxylic group, a carboxylate group, or a R9 group;

R9 represents a O—R8 group or an amino-acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

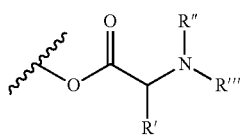

wherein R' represents an (C1-C6)alkyl group, an (C2-C6) alkenyl group, an (C2-C6)alkynyl group, a (C3-C14) cycloalkyl group, (C3-C14)cycloalkylalkyl group, a (C3-C14)cycloalkyl(C2-C6)alkenyl group, a (C3-C14) cycloalkenyl group, a (C3-C14)cycloalkenyl(C1-C6) alkyl group, a (C3-C14)cycloalkenyl(C2-C6)alkenyl group, a (C3-C14)cycloalkenyl(C2-C6)alkynyl group;

R" and R''', independently, represent hydrogen atom, an (C1-C6)alkyl group, or a nitrogen protecting group.

R8 represents a hydrogen atom, a deuterium atom, a glucuronidyl group, or a

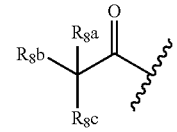

group wherein, R8a, R8b and R8c, identical or different, represent a hydrogen atom or a deuterium atom.

In a further particular embodiment, the compound of component (i) of the combination product is a compound of formula (I):

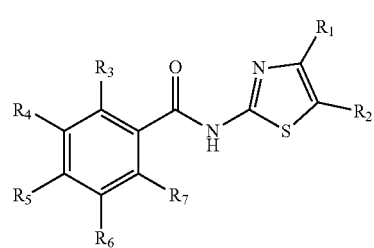

or a pharmaceutical acceptable salt thereof, in which

R1 represents a hydrogen atom (H), a deuterium atom (D), a halogen atom, a (C6-C14)aryl group, a heterocyclic group, a (C3-C14)cycloalkyl group, a (C1-C6) alkyl group, a sulfonyl group, a sulfoxyde group, a (C1-C6)alkylcarbonyl group, a (C1-C6)alkyloxy, a carboxylic group, a carboxylate group, a $NO_2$ group, a NH2 group, a (C1-C6)alkylamino group, an amido group, a (C1-C6)alkylamido group, a (C1-C6)dialkylamido group.

R2 represents a hydrogen atom, a deuterium atom, a N02 group, a (C6-C14)aryl group, a heterocyclic group, a halogen atom, a (C1-C6)alkyl group, a (C3-C14)cycloalkyl group, a (C2-C6)alkynyl group, a (C1-C6) alkyloxy group, a (C1-C6)alkylthio group, a (C1-C6) alkylcarbonyl group, a (C1-C6)alkylcarbonylamino group, a (C6-C14)arylcarbonylamino group, a carboxylic or carboxylate group, an amido group, a (C1-C6) alkylamido group, a (C1-C6)dialkylamido group, a $NH_2$ group, a (C1-C6)alkylamino group, or R1 and R2, together with the carbon atoms to which they are attached, form a substituted or unsubstituted 5- to 8-membered cycloalkyl, heterocyclic or aryl group, R3 represents a hydrogen atom, a deuterium atom, a halogen atom, a O—R8 group, a (C1-C6)alkylcarbonyl group, an (C1-C6)alkyl group, an (C1-C6)alkyloxy group, an (C1-C6)alkylthio group, an (C1-C6)alkylcarbonyloxy group, an (C6-C14)aryloxy group, a (C6-C14)aryl group, a heterocyclic group, a (C3-C14)cycloalkyl group a N02, a sulfonylaminoalkyle group, an NH2 group, an amino(C1-C6)alkyl group, an (C1-C6) alkylcarbonylamino group, a carboxylic group, a carboxylate group, an aminoacid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

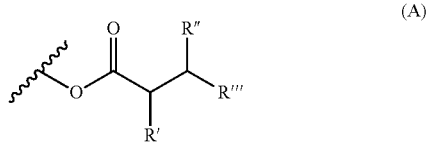

(A)

wherein R' represents an (C1-C6)alkyl group, an (C2-C6) alkenyl group, an (C2-C6)alkynyl group, a (C3-C14) cycloalkyl group, (C3-C14)cycloalkylalkyl group, a (C3-C14)cycloalkyl(C2-C6)alkenyl group, a (C3-C14) cycloalkenyl group, a (C3-C14)cycloalkenyl(C1-C6) alkyl group, a (C3-C14)cycloalkenyl(C2-C6)alkenyl group, a (C3-C14)cycloalkenyl(C2-C6)alkynyl group;
R" and R''', independently, represent hydrogen atom, an (C1-C6)alkyl group, or a nitrogen protecting group.
R8 represents a hydrogen atom, a deuterium atom, or a

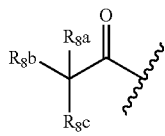

group wherein, R8a, R8b and R8c, identical or different, represent a hydrogen atom or a deuterium atom. R4, R5, R6, and R7, identical or different, represent a hydrogen atom, a deuterium atom, a halogen atom, a hydroxyl group, an (C1-C6)alkylcarbonyl group, an (C1-C6)alkyl group, an (C1-C6)alkyloxy group, an (C1-C6)alkylthio group, an (C1-C6)alkylcarbonyloxy group, an (C6-C14)aryloxy group, an (C6-C14)aryl group, a heterocyclic group, a (C3-C14)cycloalkyl group, a NO2, a sulfonylamino(C1-C6)alkyl group, an NH2 group, an amino(C1-C6)alkyl group, an (C1-C6) alkylcarbonylamino group, a carboxylic group, a carboxylate group, an aminoacid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

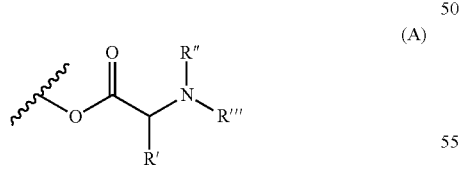

(A)

wherein R' represents an (C1-C6)alkyl group, an (C2-C6) alkenyl group, an (C2-C6)alkynyl group, a (C3-C14) cycloalkyl group, (C3-C14)cycloalkyl(C1-C6)alkyl group, a (C3-C14)cycloalkyl(C1-C6)alkenyl group, a (C3-C14)cycloalkenyl group, a (C3-C14)cycloakenyl (C1-C6)alkyl group, a (C3-C14)cycloalkenyl(C2-C6) alkenyl group, a (C3-C14)cycloalkenyl(C2-C6)alkynyl group; R" and R''', independently, represent a hydrogen atom, an (C1-C6)alkyl group, or a nitrogen protecting group;

or a pharmaceutically acceptable salt thereof.
In a particular embodiment, in the compound of formula (I) of the present invention:
- an (C1-C6)alkyl group may be a substituted or unsubstituted (C1-C6)alkyl group, in particular a substituted or unsubstituted (C1-C4)alkyl group;
- an (C2-C6)alkynyl group may be a substituted or unsubstituted (C2-C6)alkynyl group;
- a (C3-C14)cycloalkyl group may be a substituted or unsubstituted (C3-C14)cycloalkyl group
- an (C1-C6)alkyloxy group may be either substituted or unsubstituted, such as a substituted or unsubstituted (C1-C4)alkyloxy group;
- an (C1-C6)alkylthio group may be either substituted or unsubstituted, such as a substituted or unsubstituted (C1-C4)alkylthio group;
- an (C1-C6)alkylamino group may be a (C1-C4)alkylamino group;
- a (C1-C6)dialkylamino group may be a (C1-C4)dialkylamino group;
- an (C6-C14)aryl group may be a substituted or unsubstituted (C6-C14)aryl group;
- a heterocyclic group may be a substituted or unsubstituted heterocycloalkyl or heteroaryl group.

In a particular embodiment, the compound of component (i) of the combination product is a compound of formula (II)

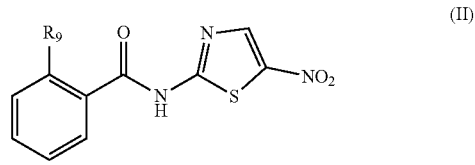

(II)

in which R9 represents a hydrogen atom, a deuterium atom, a O—R8 group (R8 is defined above), or an aminoacid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

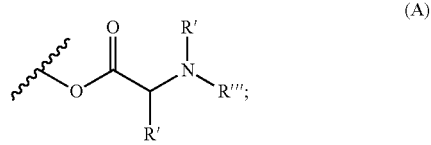

(A)

wherein R' represents an (C1-C6)alkyl group, an (C2-C6) alkenyl group, an (C2-C6)alkynyl group, a (C3-C14) cycloalkyl group, (C3-C14)cycloalkyl(C1-C6)alkyl group, a (C3-C14)cycloalkyl(C1-C6)alkenyl group, a (C3-C14)cycloalkenyl group, a (C3-C14)cycloakenyl (C1-C6)alkyl group, a (C3-C14)cycloalkenyl(C2-C6) alkenyl group, a (C3-C14)cycloalkenyl(C2-C6)alkynyl group; R" and R''', independently, represent a hydrogen atom, an (C1-C6)alkyl group, or a nitrogen protecting group or a pharmaceutically acceptable salt thereof.

In a particular embodiment, component (i) of the combination product of the invention is selected from:

NTZ:

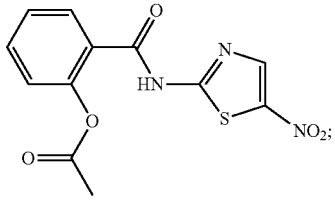 [SMILES: CC(=O)Oc1ccccc1C(=O)Nc1ncc([N+](=O)[O-])s1]

tizoxanide:

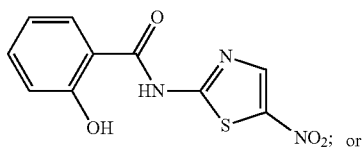 [SMILES: O=C(Nc1ncc([N+](=O)[O-])s1)c1ccccc1O]

tizoxanide glucuronide (TZG):

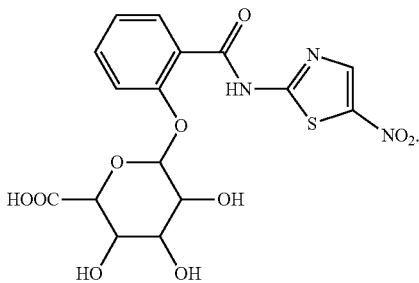 [SMILES: O=C(Nc1ncc([N+](=O)[O-])s1)c1ccccc1OC1OC(C(=O)O)C(O)C(O)C1O]

In another embodiment, component (i) of the combination product is a compound of formula (I) or (II) wherein R8 represents a hydrogen atom, a deuterium atom or a

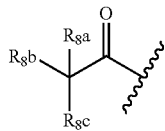

group wherein, R8a, R8b and R8c, identical or different, represent a hydrogen atom or a deuterium atom; and/or
wherein R1, R3, R4, R5, and R6, identical or different, represent a hydrogen atom or a deuterium atom with the proviso that R1, R2, R2a, R2b, R2c, R3, R4, R5, and R6 are not simultaneously a hydrogen atom.

In a particular embodiment, component (i) is [(5-nitro-1,3-thiazol-2-yl)carbamoyl]phenyl (d3)ethanoate, 2-[(5-nitro-1,3-thiazol-2-yl)carbamoyl]phenyl (d2) ethanoate; or 2-[(5-nitro-1,3-thiazol-2-yl)carbamoyl]phenyl (d1) ethanoate.

In another particular embodiment, component (i) is ((S)-2-(5-nitrothiazol-2-ylcarbamoyl)phenyl 2-amino-3,3-dimethylbutanoate hydrochloride) (RM5061) or formula:

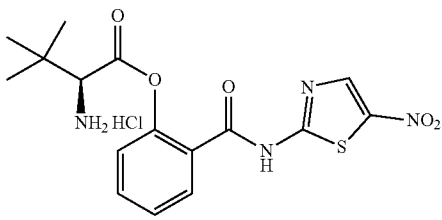 [SMILES: CC(C)(C)[C@H](N)C(=O)Oc1ccccc1C(=O)Nc1ncc([N+](=O)[O-])s1 ; Cl]

In another particular embodiment, component (i) is ((2S,3S)-2-(5-nitrothiazol-2-ylcarbamoyl)phenyl 2-amino-3-methylpentanoate hydrochloride) (RM5066) of formula:

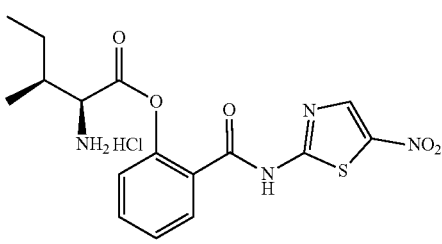 [SMILES: CC[C@H](C)[C@H](N)C(=O)Oc1ccccc1C(=O)Nc1ncc([N+](=O)[O-])s1 ; Cl]

In a further particular embodiment, the PPAR agonist is a PPAR-alpha agonist, a PPAR-gamma agonist, a PPAR-delta agonist, a PPAR-alpha/gamma dual agonist, a PPAR alpha/delta dual agonist, a PPAR gamma/delta dual agonist or PPAR alpha/gamma/delta pan agonist.

According to the invention the PPAR agonist(s) and component (i) comprised in the combination of the invention may be selected so that the combination of said PPAR agonist(s) and component (i) of the combination of the invention provides a synergistic action against inflammatory, metabolic, fibrotic and cholestatic diseases. Such synergy may be determined according to methods well-known in the art, such as by using the Excess Over Bliss (EOB) method described in the examples.

In a particular embodiment, component (ii) of the combination product is:
at least one PPAR-alpha agonist;
at least one PPAR-gamma agonist;
at least one PPAR-delta agonist;
at least one PPAR-alpha/delta dual agonist;
at least one PPAR-alpha agonist and at least one PPAR delta agonist;
at least one PPAR-alpha/gamma dual agonist;
at least one PPAR-alpha agonist and at least one PPAR gamma agonist;
at least one PPAR-gamma/delta dual agonist;
at least one PPAR-gamma agonist and at least one PPAR delta agonist;
at least one PPAR-alpha/gamma/delta pan agonist; and
at least one PPAR-alpha agonist, at least one PPAR-gamma agonist and at least one PPAR-delta agonist.

According to the present invention, the term "PPAR(s) agonists" refers the Peroxisome Proliferator Activated Receptor agonists, which are a class of drugs which plays a central role in lipid and glucose homeostasis. PPARα mainly influences fatty acid metabolism and its activation lowers lipid levels, while PPARγ is mostly involved in the regulation of the adipogenesis, energy balance, and lipid biosynthesis. PPARδ participates in fatty acid oxidation, mostly in skeletal and cardiac muscles, but it also regulates blood glucose and cholesterol levels.

According to the invention, the term "PPAR alpha agonist" as used herein includes, but is not limited to, fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, and SR10171.

According to the invention, the term "PPAR gamma agonist" as used herein includes, but is not limited to, Rosiglitazone, Pioglitazone, deuterated pioglitazone, Efatutazone, ATx08-001, OMS-405, CHS-131, THR-0921, SER-150-DN, KDT-501, GED-0507-34-Levo, CLC-3001, and ALL-4.

According to the invention, the term "PPAR delta agonist" as used herein includes, but is not limited to, GW501516 (Endurabol or ({4-[({4-methyl-2-[4-(trifluoromethyl)phenyl]-1,3-thiazol-5-yl}methyl)sulfanyl]-2-methylphenoxy}acetic acid)), MBX8025 (Seladelpar or {2-methyl-4-[5-methyl-2-(4-trifluoromethyl-phenyl)-2H-[1,2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy]acetic acid), L165041, HPP-593, and NCP-1046.

According to the invention, the term "PPAR alpha/gamma agonist" (also named glitazars) used herein includes, but is not limited to Saroglitazar, Aleglitazar, Muraglitazar, Tesaglitazar, and DSP-8658.

According to the invention, the term "PPAR alpha/delta agonist" used herein includes, but is not limited to, Elafibranor (GFT505) or T913659.

According to the invention, the term "PPAR gamma/delta agonist" used herein includes, but is not limited to a conjugated linoleic acid (CLA), T3D-959.

According to the invention, the term "PPAR alpha/gamma/delta agonist" used herein includes, but is not limited to, IVA337 (Lanifibranor), TTA (tetradecylthioacetic acid), Bavachinin, GW4148, GW9135, Bezafibrate, Lobeglitazone, and CS038. In a further embodiment, the PPAR alpha/gamma/delta agonist is 2-(4-(5,6-methylenedioxybenzo[d]thiazol-2-yl)-2-methylphenoxy)-2-methylpropanoic acid (MHY2013).

PPAR agonist may be in the form of a salt, hydrate, solvate, polymorph, or a co-crystal. PPAR agonist may also be in the form of a hydrate, solvate, polymorph, or a co-crystal of a salt.

In a more particular embodiment, the PPAR agonist is a compound of formula (III), or a pharmaceutically acceptable salt thereof:

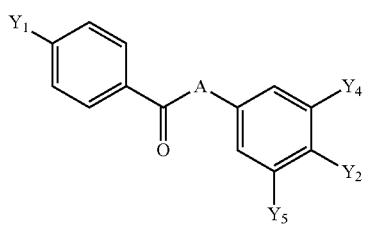

(III)

in which:
$Y_1$ represents a halogen, a Ra, or Ga—Ra group;
A represents a CH=CH or a CH2-CH2 group;
$Y_2$ represents a Gb—Rb group;

Ga and Gb, identical or different, represent an atom of oxygen or sulfur;
Ra represents a hydrogen atom, an unsubstituted (C1-C6) alkyl group, a (C6-C14)aryl group or a (C1-C6)alkyl group that is substituted by one or more halogen atoms, a (C1-C6)alkoxy or a (C1-C6)alkylthio group, (C3-C14)cycloalkyl groups, (C3-C14)cycloalkylthio groups or heterocyclic groups;
Rb represents a (C1-C6)alkyl group substituted by at least a —COORc group, wherein
Rc represents a hydrogen atom, or a (C1-C6)alkyl group that is substituted or not by one or more halogen atoms, (C3-C14)cycloalkyl groups, or heterocyclic groups; and
$Y_4$ and $Y_5$, identical or different, representing a (C1-C6) alkyl group that is substituted or not by one or more halogen atoms, (C3-C14)cycloalkyl groups or heterocyclic groups.

In a particular embodiment of the compound of formula (III):
$Y_1$ represents a halogen, a Ra, or a Ga—Ra group;
A represents a CH=CH group;
$Y_2$ represents a Gb—Rb group;
Ga and Gb, identical or different, represent an atom of oxygen or sulfur;
Ra represents a (C1-C6)alkyl or (C3-C14)cycloalkyl group, in particular a (C1-C7)alkyl or (C3-C14)cycloalkyl group substituted or not by one or more halogen atoms;
Rb represents a (C1-C6)alkyl group substituted by a —COOR3 group, wherein Rc represents a hydrogen atom or an alkyl group having from one to four carbon atoms; and
$Y_4$ and $Y_5$ independently represent a (C1-C4)alkyl group.

In a particular embodiment of the compound of formula (III):
$Y_1$ represents a Ra or Ga—Ra group;
A represents a CH2-CH2 group;
$Y_2$ represents a Gb—Rb group;
Ga represents an atom of oxygen or sulfur and Gb represents an atom of oxygen;
Ra represents a (C1-C6)alkyl or (C3-C7)cycloalkyl group;
Rb represents a (C1-C6)alkyl group substituted by at least a —COORc group, wherein
Rc represents a hydrogen atom or (C1-C4)alkyl group; and
$Y_4$ and $Y_5$ independently represent a (C1-C4)alkyl group.

In a particular embodiment of the compound of formula (III):
$Y_1$ represents a halogen atom or a Ra or Ga—Ra group;
A represents a CH2-CH2 group;
$Y_2$ represents a Gb—Rb group;
Ga represents an atom of oxygen or sulfur and Gb represents an atom of oxygen;
Ra represents a (C1-C6)alkyl or (C3-C14)cycloalkyl group that is substituted by one or more halogen atoms;
Rb represents a (C1-C6)alkyl group substituted or not by one or more halogen atoms and substituted by at least a —COORc group, wherein Rc represents a hydrogen atom or a (C1-C4)alkyl group; and
$Y_4$ and $Y_5$ represent a (C1-C4)alkyl group.

In a particular embodiment of the compound of formula (III), Gb is an oxygen atom and Rb is (C1-C6)alkyl group substituted by a —COORc group, wherein Rc represents a hydrogen atom or an unsubstituted linear or branched (C1-C4)alkyl group.

In a particular embodiment of the compound of formula (III), Y1 is a (C1-C6)alkylthio group that comprises a (C1-C6)alkyl group that is linear or branched that is substituted or not by one or more halogen atoms.

In a particular embodiment, the compound of formula (III) is selected in the group consisting of 1-[4-methylthiophenyl]-3-[3,5-dimethyl-4-carboxydimethylmethyloxy phenyl]prop-2-en-1-one (Elafibranor or GFT505), 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl] prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl] prop-2-en-1-one, 1-[4-trifluoromethyloxyphenyl]-3-[3,5-dimethyl-4-carboxydimethylmethyl oxyphenyl]prop-2-en-1-one, 2-[2,6-dimethyl-4-[3-[4-(methylthio)phenyl]-3-oxo-propyl] phenoxy]-2-methylpropanoic acid, and 2-[2,6-dimethyl-4-[3-[4-(methylthio) phenyl]-3-oxo-propyl]phenoxy]-2-methyl-propanoic acid isopropyl ester.

In a more particular embodiment, the PPAR agonist is 1-[4-methylthiophenyl]-3-[3,5-dimethyl-4-carboxydimethylmethyloxy phenyl]prop-2-en-1-one (or Elafibranor—GFT505), or a pharmaceutically acceptable salt thereof.

In a particular embodiment of the combination product of the invention:
component (ii) is selected in the group consisting of Elafibranor, Saroglitazar, Seladelpar and Lanifibranor, component (ii) being more particularly Elafibranor;
component (i) is selected from NTZ, TZ, 2-[(5-nitro-1,3-thiazol-2-yl)carbamoyl]phenyl (d3)ethanoate, 2-[(5-nitro-1,3-thiazol-2-yl)carbamoyl]phenyl (d2) ethanoate, 2-[(5-nitro-1,3-thiazol-2-yl)carbamoyl]phenyl (d1) ethanoate, ((S)-2-(5-nitrothiazol-2-ylcarbamoyl)phenyl 2-amino-3,3-dimethylbutanoate hydrochloride) or ((2S,3S)-2-(5-nitrothiazol-2-ylcarbamoyl)phenyl 2-amino-3-methylpentanoate hydrochloride).

In a further embodiment, component (i) is selected from TZG, 2-(5-nitrothiazol-2-ylcarbamoyl)phenyl 2-amino-3,3-dimethylbutanoate (such as (S)-2-(5-nitrothiazol-2-ylcarbamoyl)phenyl 2-amino-3,3-dimethylbutanoate or its hydrochloride salt), 2-(5-nitrothiazol-2-ylcarbamoyl)phenyl 2-amino-3-methylpentanoate (such as (2S,3S)-2-(5-nitrothiazol-2-ylcarbamoyl)phenyl 2-amino-3-methylpentanoate or its hydrochloride salt), 2-(5-chlorothiazol-2-ylcarbamoyl)phenyl 2-amino-3,3-dimethylbutanoate (such as (S)-2-(5-chlorothiazol-2-ylcarbamoyl)phenyl 2-amino-3,3-dimethylbutanoate or its hydrochloride salt), and 2-(5-chlorothiazol-2-ylcarbamoyl)phenyl 2-amino-3-methylpentanoate (such as (2S,3S)-2-(5-chlorothiazol-2-ylcarbamoyl)phenyl 2-amino-3-methylpentanoate or its hydrochloride salt). In a further variant of this embodiment, component (ii) is selected in the group consisting of Elafibranor, Saroglitazar Seladelpar and Lanifibranor, component (ii) being more particularly Elafibranor; and component (i) is selected from TZG, 2-(5-nitrothiazol-2-ylcarbamoyl)phenyl 2-amino-3,3-dimethylbutanoate (such as (S)-2-(5-nitrothiazol-2-ylcarbamoyl)phenyl 2-amino-3,3-dimethylbutanoate or its hydrochloride salt), 2-(5-nitrothiazol-2-ylcarbamoyl)phenyl 2-amino-3-methylpentanoate (such as (2S,3S)-2-(5-nitrothiazol-2-ylcarbamoyl)phenyl 2-amino-3-methylpentanoate or its hydrochloride salt), 2-(5-chlorothiazol-2-ylcarbamoyl)phenyl 2-amino-3,3-dimethylbutanoate (such as (S)-2-(5-chlorothiazol-2-ylcarbamoyl)phenyl 2-amino-3,3-dimethylbutanoate or its hydrochloride salt), and 2-(5-chlorothiazol-2-ylcarbamoyl)phenyl 2-amino-3-methylpentanoate (such as (2S,3S)-2-(5-chlorothiazol-2-ylcarbamoyl)phenyl 2-amino-3-methylpentanoate or its hydrochloride salt)

In a particular embodiment, the combination product of the invention further comprises at least one other therapeutically active agent such as an antifibrotic agent, an anti-inflammatory agent or an immunosuppressant agent.

Illustrative antifibrotic agents include pirfenidone or receptor tyrosine kinase inhibitors (RTKIs) such as Nintedanib, Sorafenib and other RTKIs, or angiotensin II (AT1) receptor blockers, or CTGF inhibitor, or any antifibrotic compound susceptible to interfere with the TGFβ and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type Ill receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ.

Illustrative anti-inflammatory and/or immunosuppressant agents include glucocorticoids, NSAIDS, cyclophosphamide, nitrosoureas, folic acid analogs, purine analogs, pyrimidine analogs, methotrexate, azathioprine, mercaptopurine, ciclosporin, myriocin, tacrolimus, sirolimus, mycophenolic acid derivatives, fingolimod and other sphingosine-1-phosphate receptor modulators, monoclonal and/or polyclonal antibodies against such targets as proinflammatory cytokines and proinflammatory cytokine receptors, T-cell receptor and integrins.

In a particular embodiment, the combination product of the invention is a composition comprising components (i) and (ii) as described above, and a pharmaceutically acceptable carrier.

In a particular embodiment, the combination product is a kit of parts comprising components (i) and (ii) as described above, for sequential, separate or simultaneous use.

In a further embodiment, components i) and ii) are formulated in an injectable suspension, a gel, an oil, a pill, a tablet, a suppository, a powder, a capsule, an aerosol, an ointment, a cream, a patch, or means of galenic forms for a prolonged and/or slow release.

In another embodiment, components (i) and (ii) of the combination product in the treatment of any of the diseases mentioned above.

The present invention also relates to the combination product according to the invention, for use as a medicament.

The invention also relates to the combination product herein disclosed, for use in a method for the treatment of the disease. In another embodiment, the invention relates to a method for the treatment of a disease, comprising administering to a subject in need thereof a therapeutically effective amount of the combination product herein discloses. In another embodiment, it is provided the use of a combination product according to the invention, for the manufacture of a medicament for the treatment of a disease.

In particular, the combination product of the present invention is useful for the treatment of diseases such as immune, inflammatory, metabolic, fibrotic and cholestatic diseases. In a particular embodiment, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, familial intrahepatic cholestasis type 3 (PFIC3), inflammatory bowel diseases, Crohn's disease, ulcerative colitis, keloid, old myocardial infarction, scleroderma/systemic sclerosis, inflammatory diseases, neurodegenerative diseases, cancers, liver cancer, hepatocallular carcinoma, gastrointestinal cancer, gastric cancer, meningioma associated with neurofibromatosis, pancreatic neuroendocrine tumors, pancreatic exocrine tumors, leukemia, myeloproliferative/myelodisplastic diseases, mastocytosis, dermatofibrosarcoma, solid tumors including breast, lung, thyroid or colorectal cancer, a prostate cancer, liver fibrosis or cirrhosis of any origin, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, skin fibrosis, epidermis fibrosis, endodermis fibrosis, skin fibrosis due to scleroderma/systemic sclerosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF), heart fibrosis, kidney fibrosis, nephrogenic systemic fibrosis, muscle fibrosis, soft tissue (e.g. mediastinum or retroperitoneum) fibrosis, bone marrow fibrosis, joint fibrosis, tendon fibrosis, cartilage fibrosis, pancreas fibrosis, uterus fibrosis, nervous system fibrosis, testis fibrosis, ovary fibrosis, adrenal gland fibrosis, artery fibrosis, vein fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, peri-implantational fibrosis and asbestosis, arthrofibrosis, adhesive capsulitis.

In a most preferred embodiment, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, familial intrahepatic cholestasis type 3 (PFIC3), inflammatory bowel diseases, Crohn's disease, ulcerative colitis, liver cancer, hepatocallular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF), In a further aspect, the invention relates to the combination of the invention, for use in the inhibition of proliferation and/or activation of fibroblasts responsible for the production of collagen fibers and/or responsible for the production of the extracellular matrix.

According to the present invention, the term "autoimmune diseases" is used to designate a condition that arises from an abnormal immune response of the body against substances and tissues normally present in the body. The disease may be restricted to certain organs (e.g in type I diabetes or autoimmune thyroiditis) or involve a particular tissue in different places (e.g. in Goodpasture's disease, affection of the basement membrane in the lung and the kidney).

The term "inflammation" is used to designate a condition that arise from a protective response involving host cells, blood vessels, and proteins and other mediators which may serve to eliminate the cause of cell/tissue injury, as well as the necrotic cells/tissues resulting from the original insult, and to initiate the process of repair. The inflammatory reaction may be manifested by pain, heat, redness, swelling, blood vessels dilatation, blood flow increase and loss of function.

The terms "fibrosis", "fibrotic disease", "fibrotic disorder" and declinations thereof denote a pathological condition of excessive deposition of fibrous connective tissue in an organ or tissue. More specifically, fibrosis is a pathologic process, which includes a persistent fibrotic scar formation and overproduction of extracellular matrix, by the connective tissue, as a response to tissue damage. Physiologically, the deposit of connective tissue can obliterate the architecture and function of the underlying organ or tissue.

According to the present invention, the fibrosis or fibrotic disorder may be associated with any organ or tissue fibrosis. Illustrative, non-limiting examples of particular organ fibrosis include liver, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, soft tissue (e.g. mediastinum or retroperitoneum), bone marrow, joint (e.g. knee, shoulder or other joints) or stomach fibrosis.

In a particular embodiment, the fibrotic disorder is selected in the group consisting of a liver, kidney, skin, epidermis, endodermis, muscle, tendon, cartilage, heart, pancreas, lung, uterus, nervous system, testis, ovary, adrenal gland, artery, vein, colon, intestine (e.g. small intestine), biliary tract, soft tissue (e.g. mediastinum or retroperitoneum), bone marrow, joint (e.g. knee, shoulder or other joints), eye or stomach fibrosis.

In a preferred embodiment, the fibrotic disorder is selected in the group consisting of a liver, gut, lung, heart, kidney, muscle, skin, soft tissue (e.g. mediastinum or retroperitoneum), bone marrow, intestinal, and joint (e.g. knee, shoulder or other joints) fibrosis.

In a more preferred embodiment, the fibrotic disorder is selected in the group consisting of the liver, lung, intestinal, heart, skin, kidney and intestinal fibrosis.

In another embodiment, the fibrotic disorder is selected in the group consisting of liver, lung, heart and intestinal fibrosis. In a more particular embodiment, the fibrotic disorder is selected in the group consisting of liver, lung, skin, kidney and intestinal fibrosis. In another embodiment, the fibrotic disorder is liver fibrosis.

In a more preferred embodiment of the present invention, treated fibrotic disorder is selected in the group consisting of the following non exhaustive list of fibrotic disorders: non-alcoholic steatohepatitis (NASH), pulmonary fibrosis, idiopathic pulmonary fibrosis, skin fibrosis, eye fibrosis (such as capsular fibrosis), endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, lung fibrosis consecutive to chronic inflammatory airway disease (COPD, asthma, emphysema, smoker's lung, tuberculosis, IPF), alcohol or drug-induced liver fibrosis, liver cirrhosis, infection-induced liver fibrosis, radiation or chemotherapeutic-induced fibrosis, nephrogenic systemic fibrosis, Crohn's disease, ulcerative colitis, keloïd, old myocardial infarction, scleroderma/systemic sclerosis, arthrofibrosis, some forms of adhesive capsulitis, chronic fibrosing cholangiopathies such as Primary Sclerosing Cholangitis (PSC) and Primary Biliary Cholangitis (PBC), biliary atresia, familial intrahepatic cholestasis type 3 (PFIC3), peri-implantational fibrosis and asbestosis.

Cholestasis is defined as a decrease in bile flow due to impaired secretion by hepatocytes (hepato-cellular cholestasis) or to obstruction of bile flow through intra- or extrahepatic bile ducts (obstructive cholestasis). In clinical practice, cholestasis is any condition in which the flow of bile from the liver is slowed or blocked. According to a particular embodiment of the invention, the cholestestatic disease is selected in the group consisting of primary biliary cholangitis (PBC), primary sclerosing cholangitis (PSC), Intrahepatic Cholestasis of Pregnancy, Progressive Familial Intrahepatic Cholestasis, Biliary atresia, Cholelithiasis, Infectious Cholangitis, Cholangitis associated with Langerhans cell histiocytosis, Alagille syndrome, Nonsyndromic ductal paucity, Drug-induced cholestasis, and Total parenteral nutrition-associated cholestasis. In a preferred embodiment, the cholestatic disease is PBC or PSC, in particular PBC.

Examples of inflammatory diseases, fibrotic diseases, metabolic diseases and cholestatic diseases include metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, familial intrahepatic cholestasis type 3 (PFIC3), inflammatory bowel diseases, Crohn's disease, ulcerative colitis, keloid, old myocardial infarction, scleroderma/systemic sclerosis, inflammatory diseases, neurodegenerative diseases, cancers, liver cancer, hepatocallular carcinoma, gastrointestinal cancer, gastric cancer, meningioma associated with neurofibromatosis, pancreatic neuroendocrine tumors, pancreatic exocrine tumors, leukemia, myeloproliferative/myelodisplastic diseases, mastocytosis, dermatofibrosarcoma, solid tumors including breast, lung, thyroid or colorectal cancer, a prostate cancer, liver fibrosis or cirrhosis of any origin, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, skin fibrosis, epidermis fibrosis, endodermis fibrosis, skin fibrosis due to scleroderma/systemic sclerosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF), heart fibrosis, kidney fibrosis, nephrogenic systemic fibrosis, muscle fibrosis, soft tissue (e.g. mediastinum or retroperitoneum) fibrosis, bone marrow fibrosis, joint fibrosis, tendon fibrosis, cartilage fibrosis, pancreas fibrosis, uterus fibrosis, nervous system fibrosis, testis fibrosis, ovary fibrosis, adrenal gland fibrosis, artery fibrosis, vein fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, peri-implantational fibrosis and asbestosis, arthrofibrosis, adhesive capsulitis.

Preferably, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, familial intrahepatic cholestasis type 3 (PFIC3), inflammatory bowel diseases, Crohn's disease, ulcerative colitis, liver cancer, hepatocallular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF).

The term "treatment" or "treating" refers to the curative or preventive of a fibrotic disorder in a subject in need thereof. The treatment involves the administration of the combination of the invention to a subject having a declared disorder, i.e. to a patient, to prevent, cure, delay, reverse, or slow down the progression of the disorder, improving thereby the condition of the subject. A treatment may also be administered to a subject that is healthy or at risk of developing a fibrotic disorder.

Therefore, according to the invention, the treatment of a immune, inflammatory, metabolic, fibrotic and cholestatic disease involves the administration of the combination of the present invention, for example in the form of a pharmaceutical composition containing components (i) and (ii) of the combination, to a subject having a declared disorder to cure, delay, reverse or slow down the progression of the disorder, thus improving the condition of the patient or to a healthy subject, in particular a subject who is at risk of developing such disease.

The treatment involves the administration of the combination of the invention to a patient having a declared disorder to cure, delay, or slow down the progress, thus improving the condition of the patient or to a healthy subject, in particular a subject who is at risk of developing an inflammatory, metabolic, fibrotic and cholestatic disease.

The subject to be treated is a mammal, preferably a human. The subject to be treated according to the invention can be selected on the basis of several criteria associated to fibrotic diseases such as previous drug treatments, associated pathologies, genotype, exposure to risk factors, viral infection, as well as on the basis of the detection of any relevant biomarker that can be evaluated by means of imaging methods and immunological, biochemical, enzymatic, chemical, or nucleic acid detection methods.

The subjects to be treated according to the invention can be selected on the basis of several criteria associated to inflammatory, metabolic, fibrotic and cholestatic diseases such as previous drug treatments, associated pathologies, genotype, exposure to risk factors, viral infection, as well as any other relevant biomarker that can be evaluated by means of imaging methods and immunological, biochemical, enzymatic, chemical, or nucleic acid detection method.

Synthesis of NTZ or analogues can be for example carried out as described in (Rossignol and Cavier, 1975), or by any other way of synthesis known by a person skilled in the art.

In a particular embodiment, the treatment of an inflammatory, metabolic, fibrotic and cholestatic disease may comprise the administration of a composition comprising at least two compounds selected from NTZ and NTZ analogues. In this embodiment, the administered at least one PPAR agonist is provided in the same composition as the two compounds, or in a separate form, such as in a different composition.

In another embodiment, the combination of the invention is for simultaneous, sequential or separate administration in therapy, therefore being possibly included in different compositions. In case of sequential administration, NTZ and/or NTZ analogue(s) may be administrated prior to the PPAR agonist(s), or the PPAR agonist(s) is (are) administrated prior to NTZ and/or NTZ analogue(s).

NTZ and NTZ analogue(s) can be formulated as pharmaceutically acceptable salts, particularly acid or base salts compatible with pharmaceutical use. Salts of NTZ and NTZ analogue(s) include pharmaceutically acceptable acid addition salts, pharmaceutically acceptable base addition salts, pharmaceutically acceptable metal salts, ammonium and alkylated ammonium salts. These salts can be obtained during the final purification step of the compound or by incorporating the salt into the previously purified compound.

Combination of a compound of Formula (I) or (II) with one or more PPAR agonist(s) can be formulated as pharmaceutically acceptable non-toxic salts obtained from organic or inorganic bases or acids of compound of Formula (I) or (II) or PPAR agonist(s). These salts can be obtained during the final purification step of the compound or by incorporating the salt into the previously purified compound.

The pharmaceutical compositions of the present invention comprising a compound of Formula (I) or (II) and one or more PPAR agonist(s) can also comprise one or several excipients or vehicles, acceptable within a pharmaceutical context (e.g. saline solutions, physiological solutions, isotonic solutions, etc., compatible with pharmaceutical usage and well-known by one of ordinary skill in the art).

These compositions can also comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc.

These compositions can be formulated in the form of injectable suspensions, gels, oils, ointments, pills, suppositories, powders, gel caps, capsules, aerosols, etc., eventually by means of galenic forms or devices assuring a prolonged and/or slow release. For this kind of formulation, agents such as cellulose, carbonates or starches can be advantageously used.

The pharmaceutical compositions of the present invention comprising a compound of Formula (I) or (II) and one or more PPAR agonist(s) may be administered by different routes and in different forms. For example, the compound(s) may be administered via a systemic way, per os, parenterally, by inhalation, by nasal spray, by nasal instillation, or by injection, such as for example intravenously, by intra-muscular route, by subcutaneous route, by transdermal route, by topical route, by intra-arterial route, etc.

Of course, the route of administration will be adapted to the form of NTZ and/or NTZ analogue(s) in combination with one or more PPAR agonist(s) according to procedures well known by those skilled in the art.

NTZ and/or NTZ analogue(s) in combination with one or more PPAR agonist(s) is administered in a therapeutically effective amount. Within the context of the invention, the term "effective amount" refers to an amount of the compound sufficient to produce the desired therapeutic result.

The frequency and/or dose relative to the administration can be adapted by one of ordinary skill in the art, in function of the patient, the pathology, the form of administration, etc. Typically, the combination (such as in the form of a pharmaceutical composition or a kit-of-parts) of the present invention can be administered for the treatment of a fibrotic disease at a dose for NTZ, or a NTZ analogue or a PPAR agonist, such as a compound of Formula (I) or (II) or (Ill), comprised between 0.01 mg/day to 4000 mg/day, such as from 50 mg/day to 2000 mg/day, and particularly from 100 mg/day to 1000 mg/day.

The dose of the PPAR agonist(s) in the said combination may vary according to the PPAR agonist itself. The dose is adapted to the efficiency of the PPAR agonist.

In a preferred embodiment of the invention, NTZ is used in combination with Elafibranor at a dose comprised between 100 mg/day and 1000 mg/day (such as 1000 mg/day) (in particular 20 mg/day to 40 mg/day) for NTZ and 80 to 120 mg/day for Elafibranor.

In another preferred embodiment, the active ingredients are administered as one or more pharmaceutical composition(s) in the form of a pill intended for an oral ingestion.

Administration can be performed daily or even several times per day, if necessary.

The invention is further described with reference to the following, non-limiting, examples.

DESCRIPTION OF THE FIGURES AND TABLES

FIG. 1: Antifibrotic effect of Elafibranor and Nitazoxanide in TGFβ-induced hHSC Serum-deprived HSC were preincubated for 1 hour with Elafibranor (A) or Nitazoxanide (B), or Bezafibrate (C) before the activation with the profibrogenic cytokine TGFβ1 (1 ng/ml). After 48 hours of incubation, the expression of α-SMA was measured by ELISA. The obtained values were transformed into percentage inhibition over TGFβ1 control. Data are presented as mean (triplicates)±standard deviation (SD)]. The curve fitting and the calculation of half maximal inhibitory concentration ($IC_{50}$) were performed with XLFit software 5.3.1.3.

Figure 2:
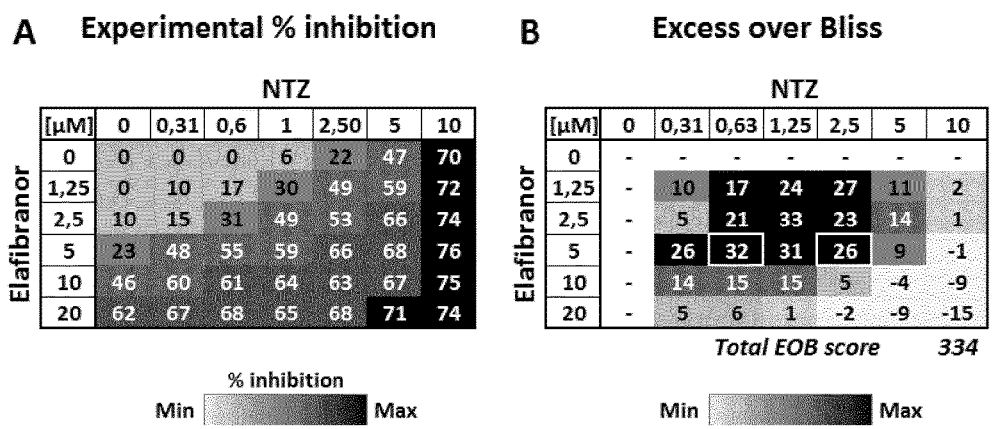
Figure 2:
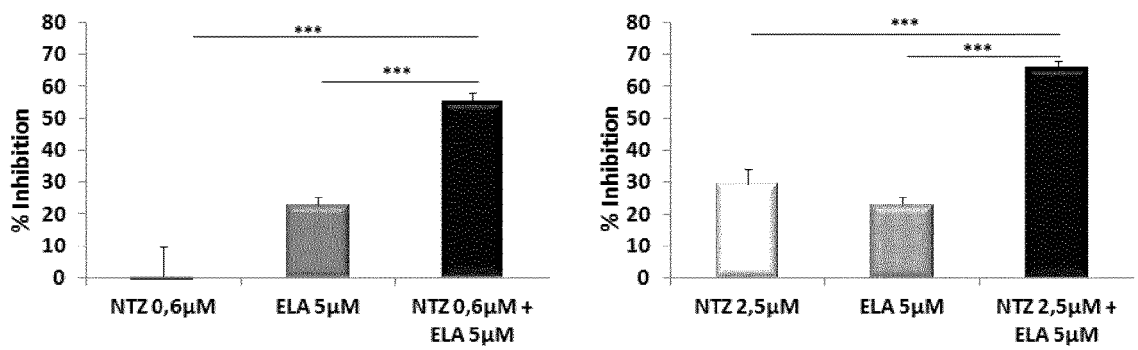

FIG. 2: Combination of Elafibranor with Nitazoxanide synergistically inhibits α-SMA in TGFβ1-induced hHSC Combinations were tested in a dose-response matrix format and analyzed according to the excess over Bliss (EOB) additivism model. Dilution series of Elafibranor (row) and Nitazoxanide (column) were prepared, including their respective DMSO controls. The resulting mixes were added to serum-deprived HSC, 1 hour prior to the activation with the profibrogenic cytokine TGFβ1 (1 ng/ml). (A) Percentage of α-SMA inhibition over the TGFβ1 control for all combination pairs. Data are presented as mean of quadruplicates. (B) EOB scores were calculated as described in Materials and Methods. Any compound pair with positive EOB value were considered synergistic (colored from light grey to black). The total EOB score including all combinations was also calculated. (C) Data values derived from a synergistic combination pair were plotted in a bar graph representation. Data are presented as mean (quadruplicates)±standard deviation (SD). EOHSA model was used as described in the Materials and Methods section to confirm the synergism of the selected NTZ/ELA combination pairs.

Figure 3:
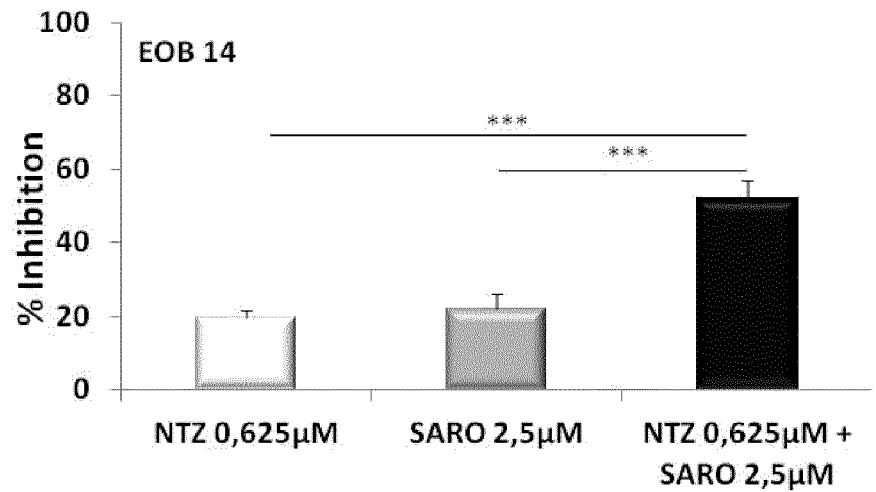
Figure 3:
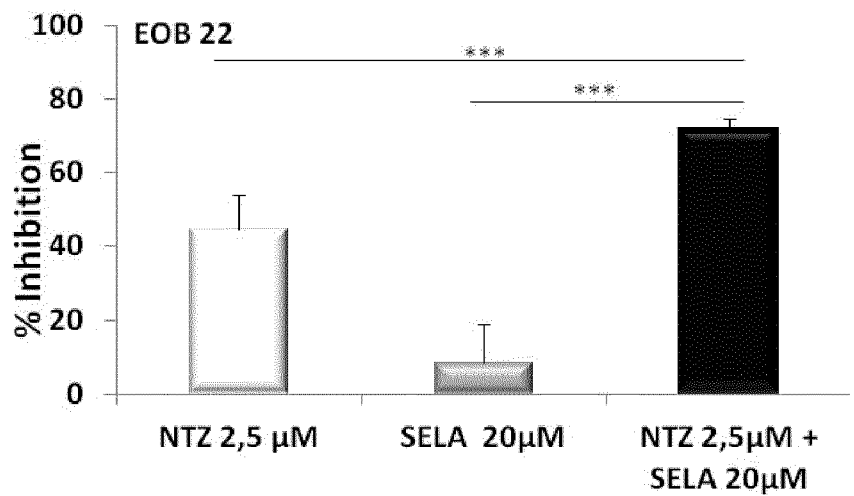
Figure 3:
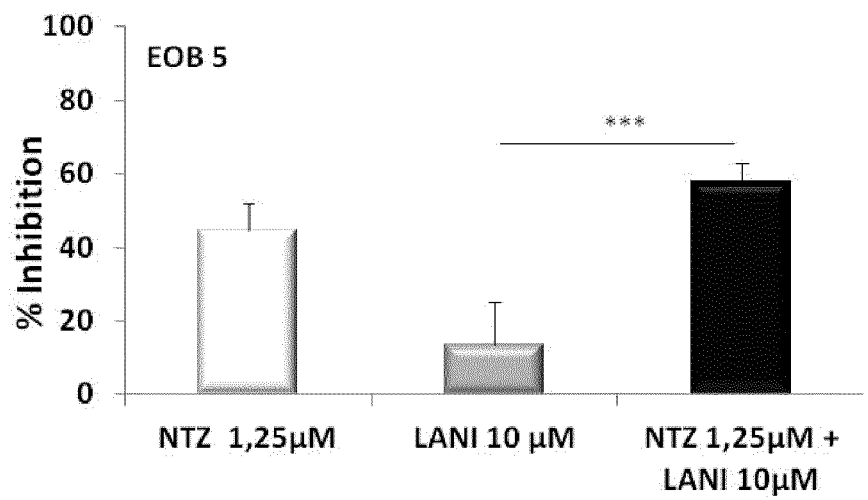

FIG. 3: Combination of PPAR agonists with Nitazoxanide synergistically inhibits α-SMA in TGFβ1-induced hHSC Combinations were tested in a dose-response matrix format and analyzed according to the excess over Bliss (EOB) additivism model. Dilution series of Saroglitazar, Seladelpar and Lanifibranor, and Nitazoxanide were prepared, including their respective DMSO controls. The resulting mixes were added to serum-deprived HSC, 1 hour prior to the activation with the profibrogenic cytokine TGFβ1 (1 ng/ml). Percentage of α-SMA inhibition over the TGFβ1 control for all combination pairs was calculated. EOB scores were calculated as described in Materials and Methods. Any compound pair with positive EOB value were considered synergistic (colored from light grey to black).

(A) Sarogliazar (SARO)
(B) Seladelpar (SELA)
(C) Lanifibranor (LANI)

Percentage of α-SMA inhibition over the TGFβ1 control derived from a synergistic combination pair were plotted in a bar graph representation. Data are presented as mean (quadruplicates)±standard deviation (SD). EOHSA model was used as described in the Materials and Methods section to confirm the synergism of the combination pairs.

Figure 4:
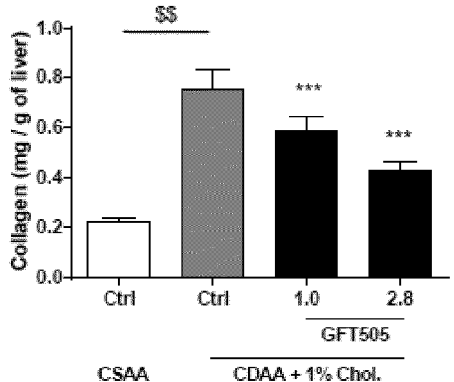
Figure 4:
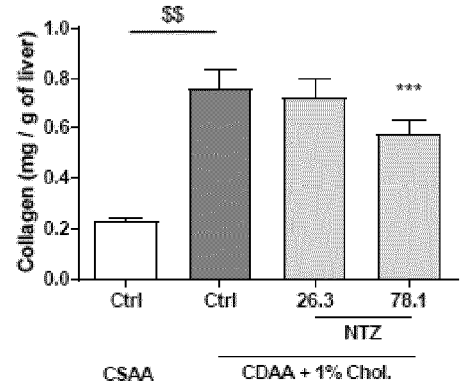
Figure 4:
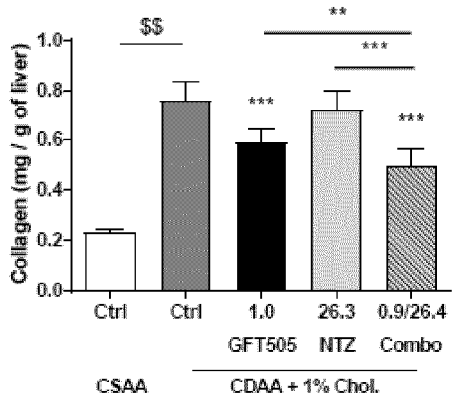
Figure 4:
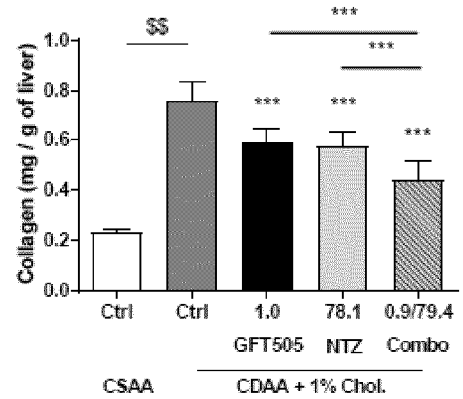
Figure 4:
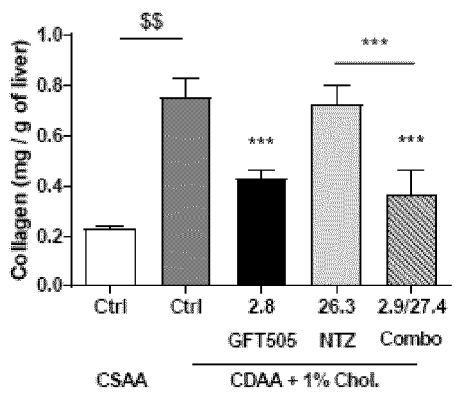
Figure 4:
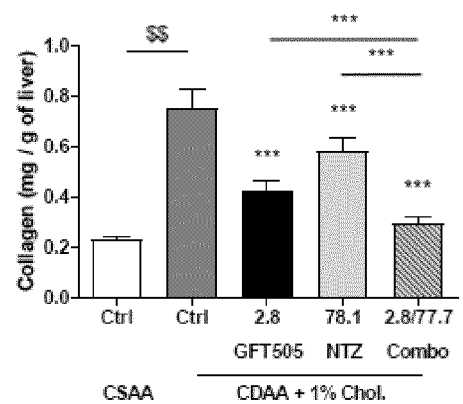

FIG. 4: Hepatic collagen content 6 week-old C57BL/6 mice were fed a control (CSAA) diet, CDAA+1% CHOL (CDAAc) diet, or CDAAc diet supplemented with NTZ (30 mg/kg/day or 100 mg/kg/day for 12 weeks) or Elafibranor (1 mg/kg/day or 3 mg/kg/day) or a combination of Elafibranor and NTZ (respectively 1+30 mg/kg/day, 1+100 mg/kg/day, 3+30 mg/kg/day and 3+100 mg/kg/day). For each graph the exact amount of exposure doses was indicated.

After the sacrifice, the hepatic collagen content was determined.

Figure 5:
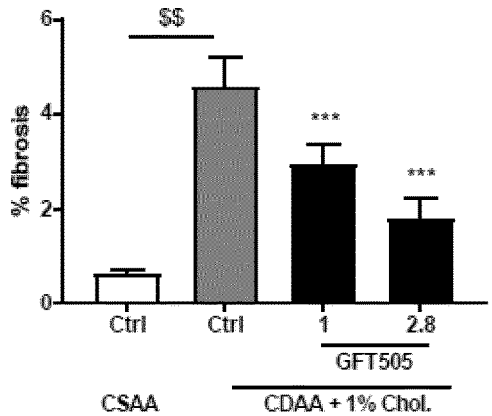
Figure 5:
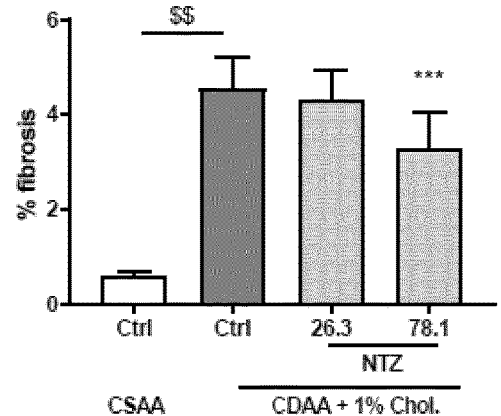
Figure 5:
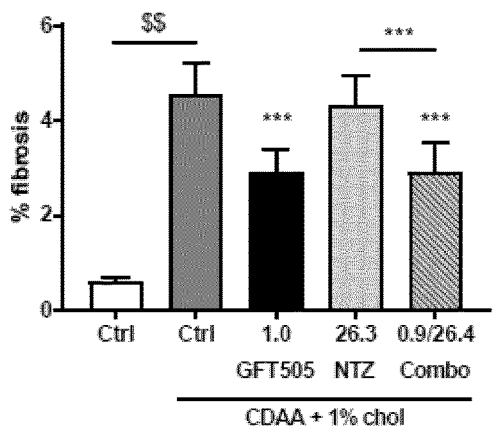
Figure 5:
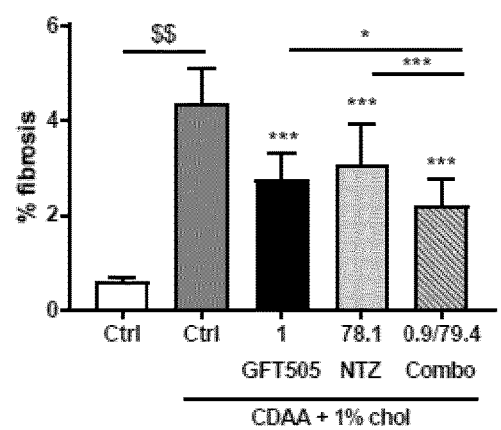
Figure 5:
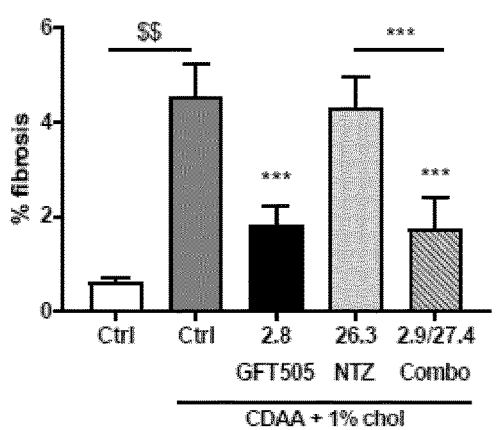
Figure 5:
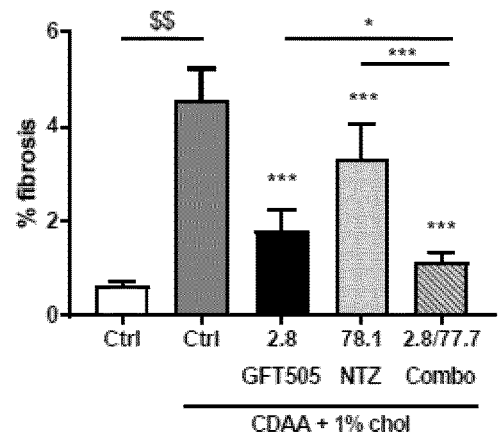

FIG. 5: Hepatic fibrosis percentage 6 week-old C57BL/6 mice were fed a control (CSAA) diet, CDAA+1% CHOL (CDAAc) diet, or CDAAc diet supplemented with NTZ (30 mg/kg/day or 100 mg/kg/day for 12 weeks) or Elafibranor (1 mg/kg/day or 3 mg/kg/day) or a combination of Elafibranor and NTZ (respectively 1+30 mg/kg/day, 1+100 mg/kg/day, 3+30 mg/kg/day and 3+100 mg/kg/day). For each graph the exact amount of exposure doses was indicated.

After the sacrifice, the hepatic fibrosis area was determined.

Figure 6:
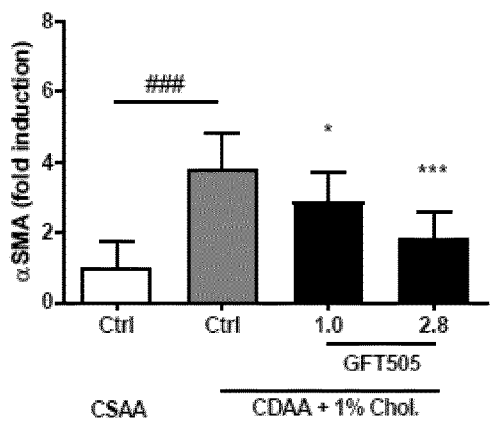
Figure 6:
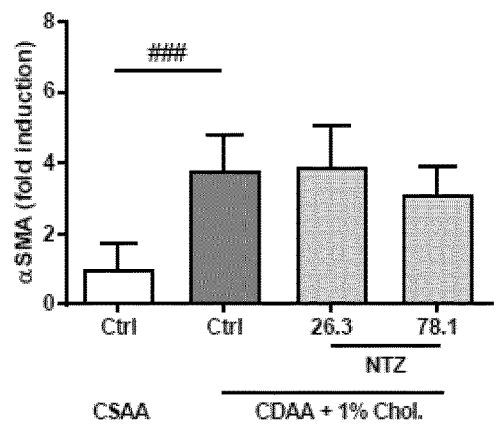
Figure 6:
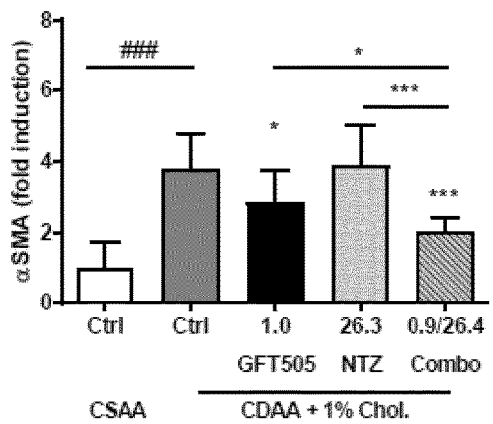
Figure 6:
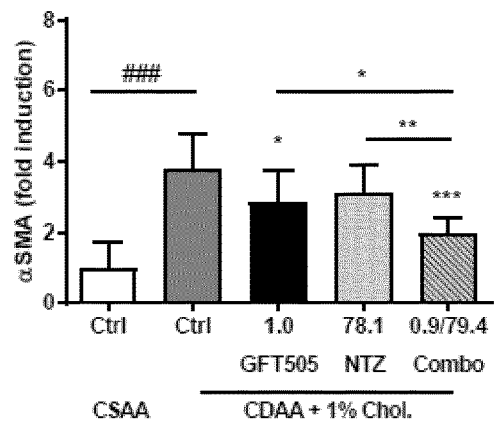
Figure 6:
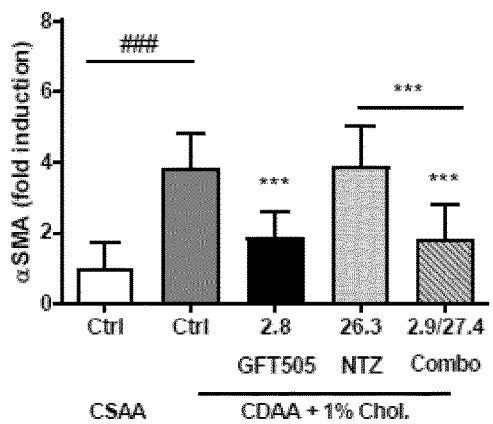
Figure 6:
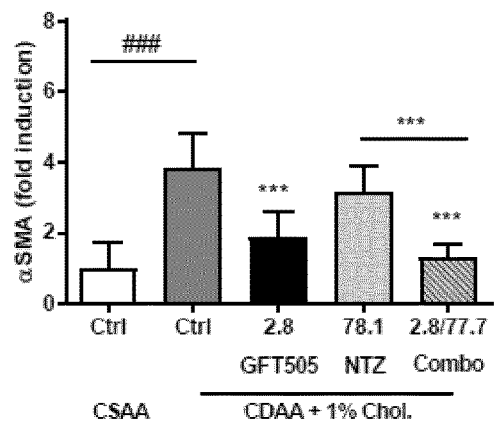
Figure 7:
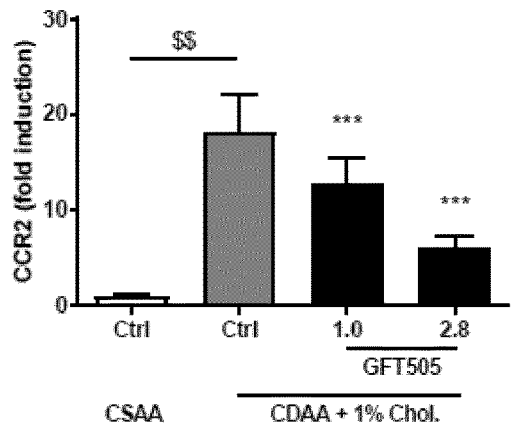
Figure 7:
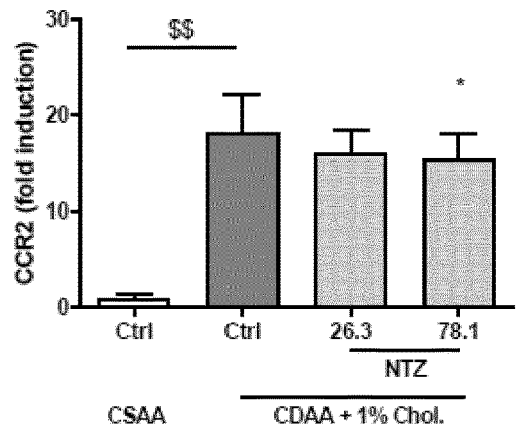
Figure 7:
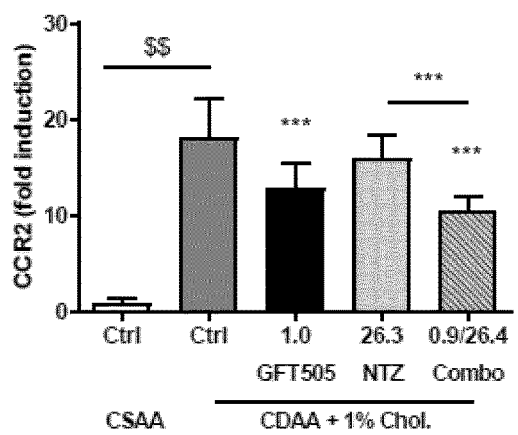
Figure 7:
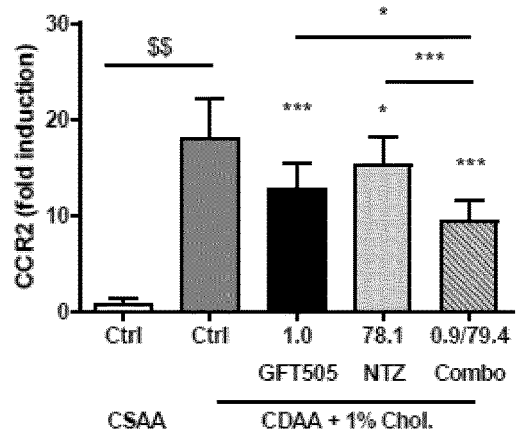
Figure 7:
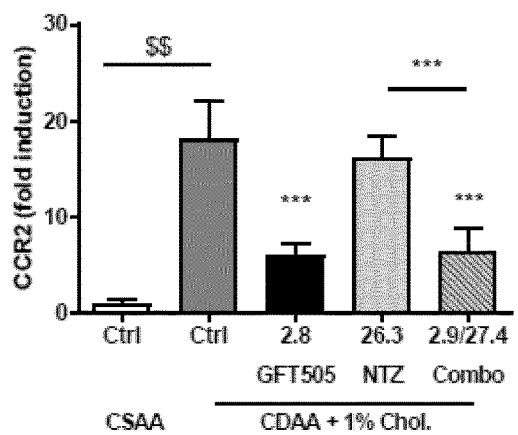
Figure 7:
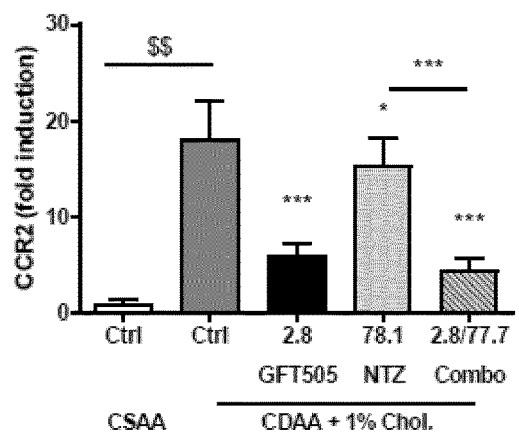
Figure 8:
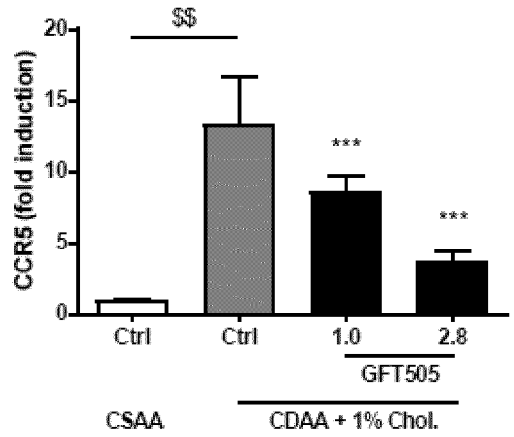
Figure 8:
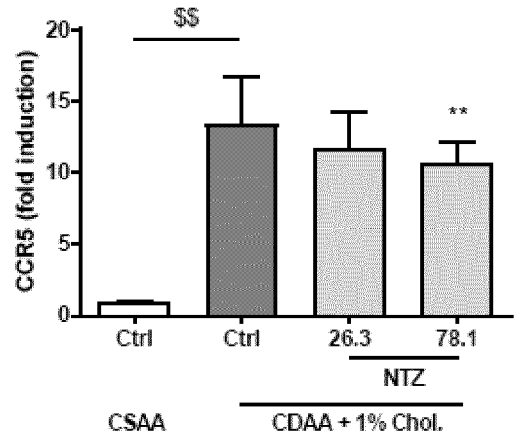
Figure 8:
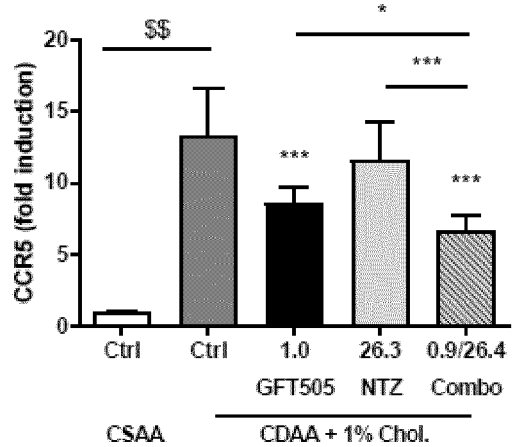
Figure 8:
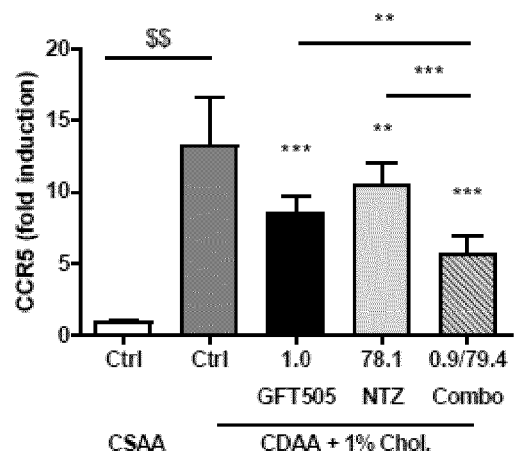
Figure 8:
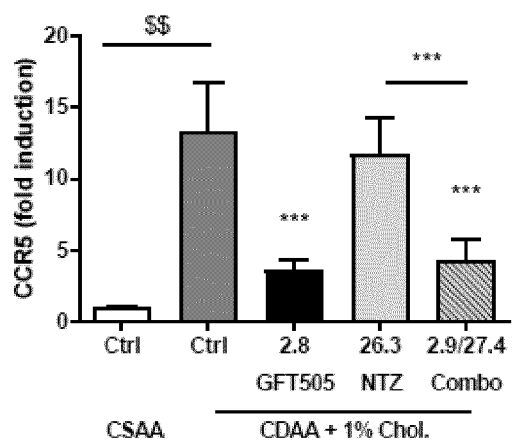
Figure 8:
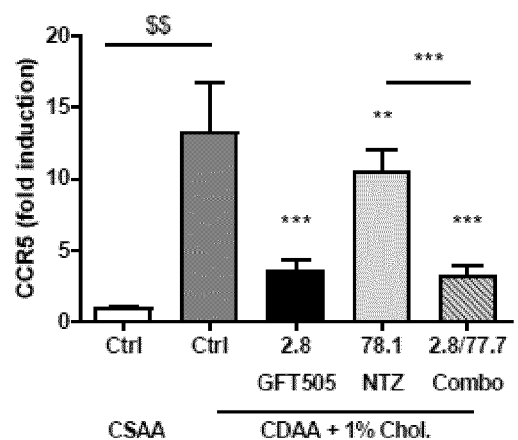
Figure 9:
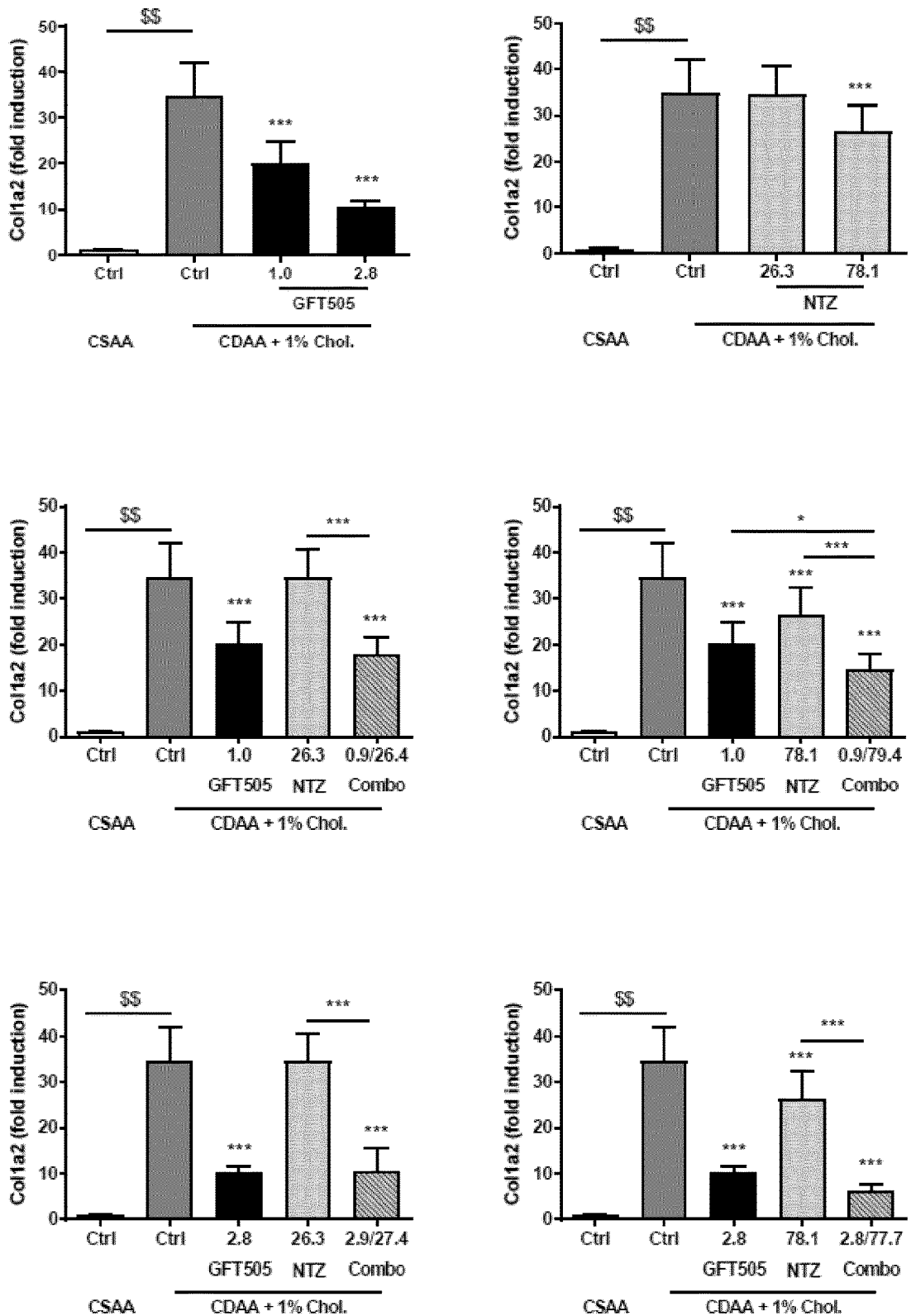
Figure 10:
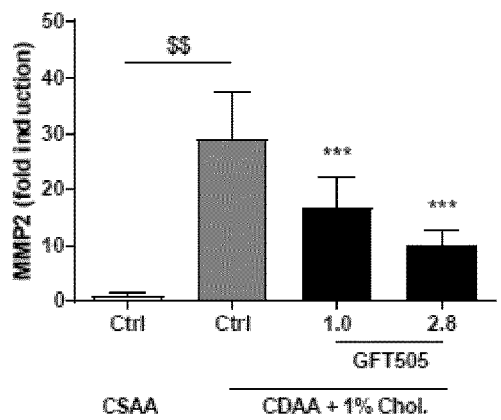
Figure 10:
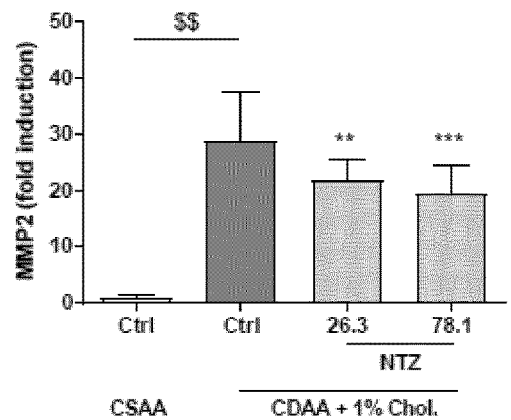
Figure 10:
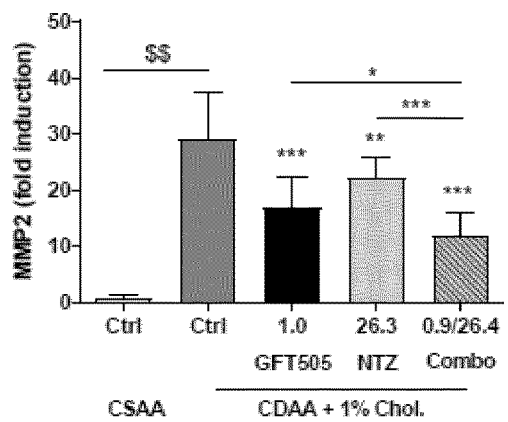
Figure 10:
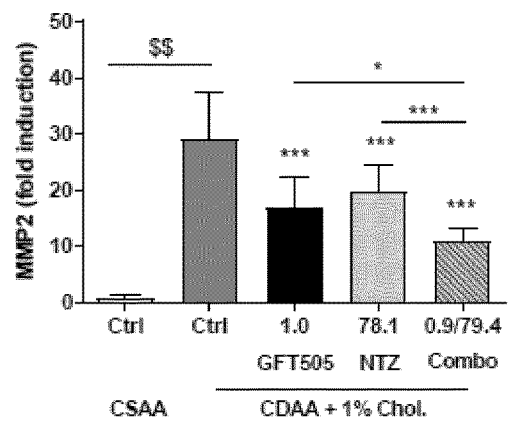
Figure 10:
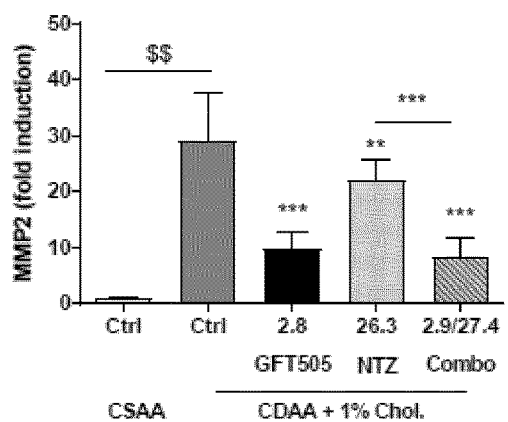
Figure 10:
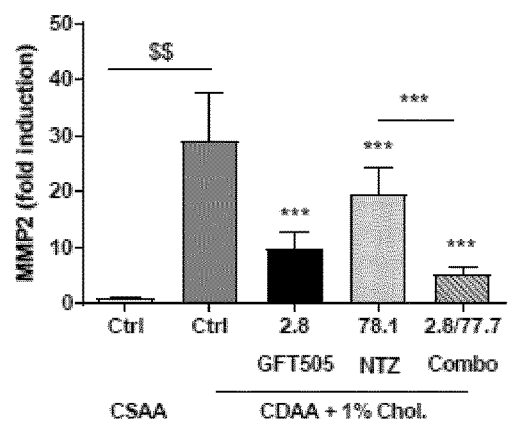
Figure 11:
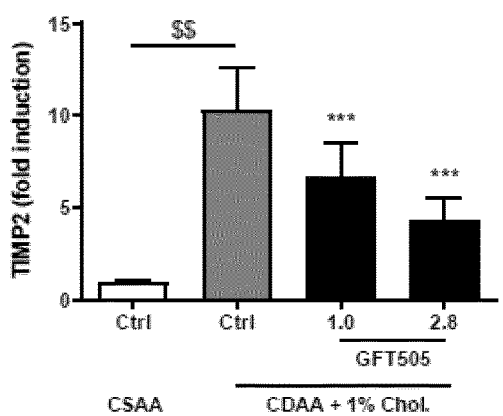
Figure 11:
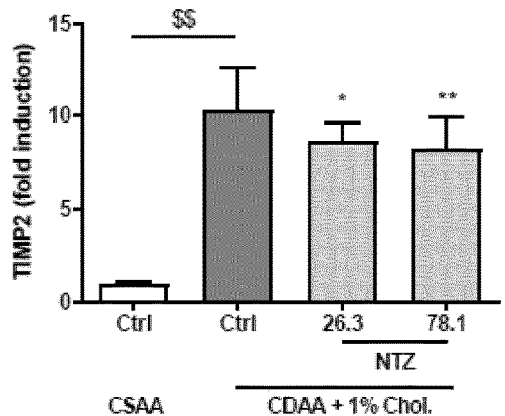
Figure 11:
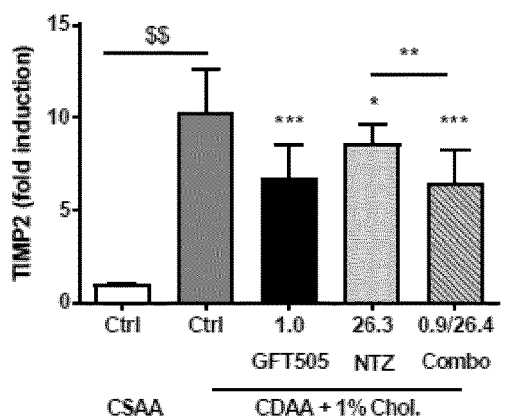
Figure 11:
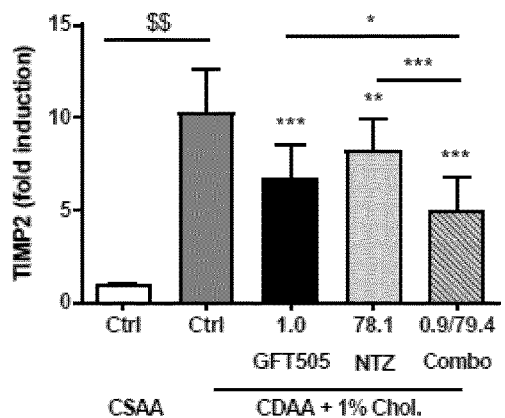
Figure 11:
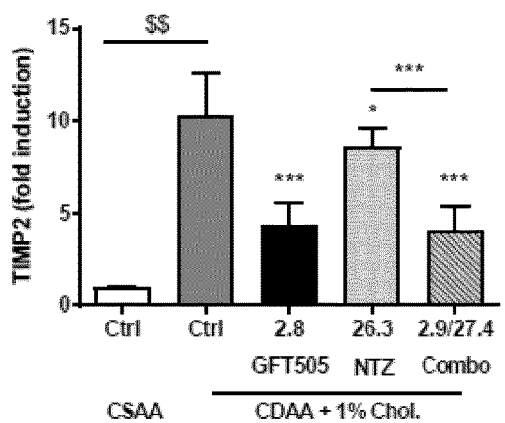
Figure 11:
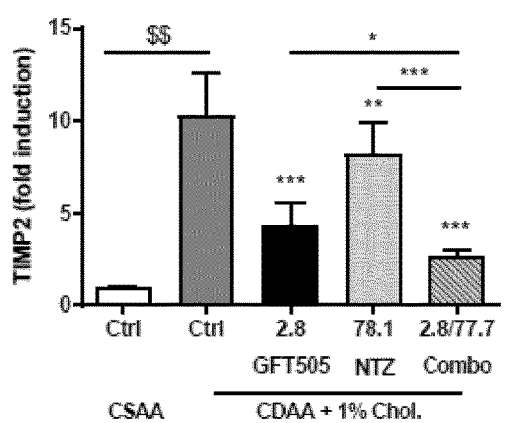
Figure 12:
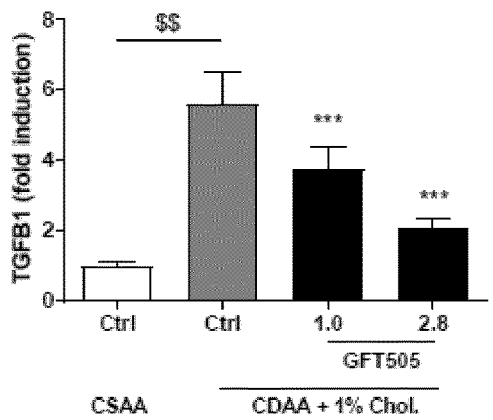
Figure 12:
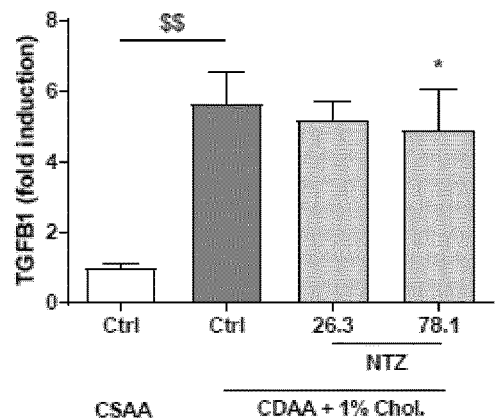
Figure 12:
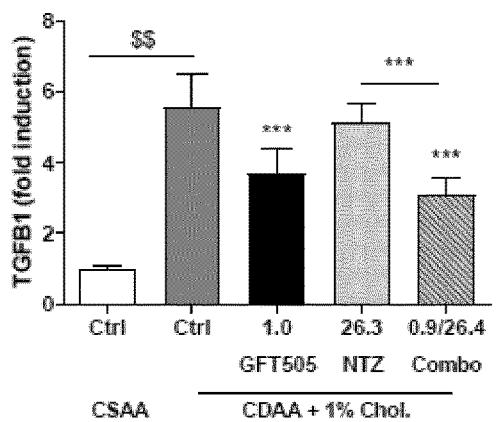
Figure 12:
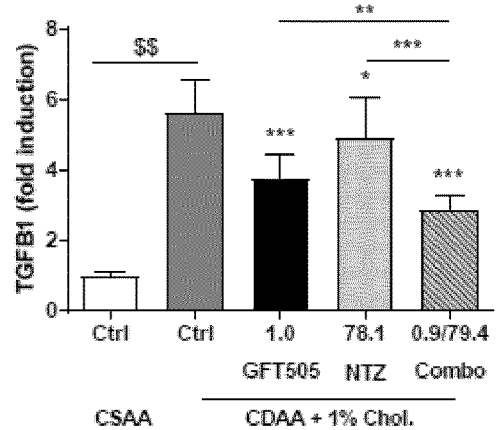
Figure 12:
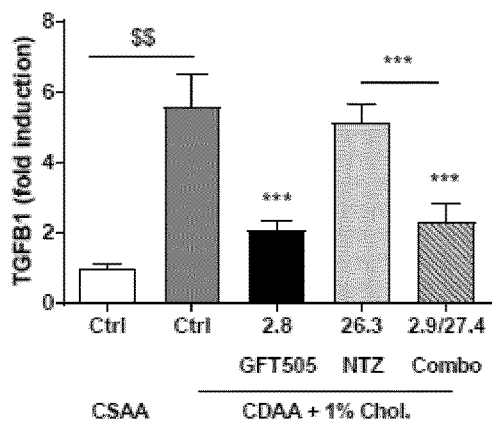
Figure 12:
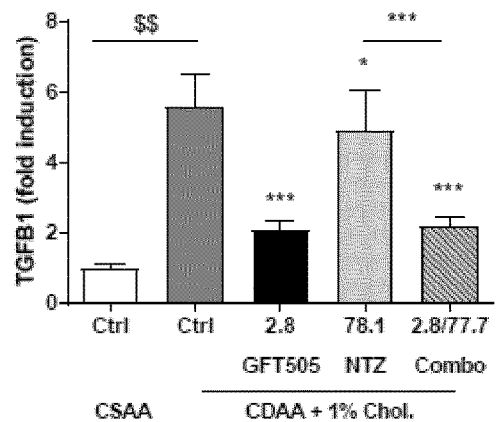

FIG. 6: Hepatic αSMA gene expression
FIG. 7: Hepatic CCR2 gene expression
FIG. 8: Hepatic CCR5 gene expression
FIG. 9: Hepatic Col1a2 gene expression
FIG. 10: Hepatic MMP2 gene expression
FIG. 11: Hepatic TIMP2 gene expression
FIG. 12: Hepatic TGFβ1 gene expression

ABBREVIATIONS USED IN THE FIGURES, IN THE TABLES, AND IN THE TEXT

AP-1 activator protein 1
ASBTi apical sodium-codependent bile acid transporter inhibitor
ASK1 signal-regulating kinase 1
AT1 angiotensin 1
COPD Chronic Obstructive Pulmonary Disease
CTGF connective tissue growth factor
DGAT diacylglycerol-O-acyltransferase
DMSO dimethylsulfoxyde
DNA desoxyribonucleic acid
DPP4 dipeptidyl peptidase
ELISA Enzyme-Linked Immuno Assay
EOB excess over Bliss
FABAC Fatty acid bile acid conjugate
FBS fetal bovine serum
FGF Fibroblast Growth Factor
FXR Farnesoid X receptor
GDF growth differentiation factor GLP-1 Glucagon-like peptide-1
GPCR G-protein coupled receptor
HBV hepatitis B virus
HCV hepatitis C virus
15-HEPE 5-hydroxyeicosapentaenoic acid
HIV human immunodeficiency virus
HSC hepatic stellate cell
IC50 half maximal inhibitory concentration
iNOS inducible nitric oxide synthase
IPF idiopathic pulmonary fibrosis
LANI Lanifibranor
LBD ligand binding domain
LPS lipopolysaccharide
LT leukotriene
MAPK Mitogen-activated protein kinase
MMP-9 metalloprotease 9
MMPase metalloprotease
NADPH nicotinamide adenine dinucleotide phosphate
NAFLD non-alcoholic fatty liver disease
NASH non-alcoholic steatohepatitis
NF-κB nuclear factor-kappa B
NOX NADPH oxidase
NSAIDs non-steroid anti-inflammatory drugs
NTZ Nitazoxanide
PAR Protease-activated receptor
PBC Primary Biliary Cholangitis
PDE phosphodiesterase
PDGF platelet-derived growth factor
PFIC3 familial intrahepatic cholestasis type 3
PFOR pyruvate:ferredoxin oxidoreductase
PPAR peroxisome proliferator activated receptor
PPRE PPAR Response Elements
PSC Primary Sclerosing Cholangitis
ROCK Rho-associated protein kinase
RTK receptor tyrosine kinase
SARO Saroglitazar
SD standard deviation
SELA Seladelpar
SGLT Sodium-glucose transport
STAT Signal Transducers and Activators of Transcription
TGFβ transforming growth factor β
TGFBRI TGFβ receptors type 1
TGFBRII TGFβ receptors type II
THBS1 Thrombospondin 1
THR p thyroid receptor 1
TIMP tissue inhibitor of metalloprotease
TLR-4 Toll Like Receptor 4
TZ Tizoxanide
TZG Tizoxanide glucuronide
VAP-1 vascular adhesion protein-1

EXAMPLES

Materials and Methods

Compounds were dissolved in dimethyl sulfoxide (DMSO, Fluka cat #41640). Nitazoxanide (INTERCHIM cat #RQ550U), tizoxanide (INTERCHIM cat #RP253), Lanifibranor (ARK PHARM cat #AK689102), Seladelpar (ARK PHARM cat #AK689146) and Saroglitazar (CHEMEXPRESS cat #YY-1997A) were obtained commercially.

hHSC Culture

The human primary hepatic stellate cells (hHSC) (Innoprot) were cultured in STeCM medium (ScienCell cat #5301) that was supplemented with 2% fetal bovine serum (FBS, ScienCell cat #0010), 1% penicillin/streptomycin (ScienCell cat #0503) and stellate cell growth supplement (SteCGS; ScienCell cat #5352). Cell-culture flasks were coated with Poly-L Lysine (Sigma cat #P4707) for a better adherence.

Preparation of Compositions

2 Components Combination Matrix (NTZ/Elafibranor)

For these experiments, a checkerboard matrix was generated. NTZ and Elafibranor stocks were serially diluted in DMSO in 5-points series in a row (PPAR agonist Elafibranor) and a 6-points series in a column NTZ) of a 96-well plate or a 384-well plate. Subsequently, the 5×6 combination matrix was generated by 1:1 mixing of all single agent concentrations. The test concentrations for each compound were chosen based on the respective $IC_{50}$ of each compound as single agent obtained by measuring α-SMA content in the HSC model stimulated with TGF-β1.

Then, 2-fold and 4-fold higher and lower concentrations were selected.

Activation of hHSC with TGF-β1 and Compound Treatment

The human primary hepatic stellate cells (hHSC) (Innoprot) were cultured under standard conditions, as described above. The cells were subsequently plated at a density of $2×10^4$ cells/well into 96-well plates and 6 500 cells/well into 384-well plates for the measure of α-SMA by ELISA. The next day, cell-culture medium was removed, and cells were washed with Phosphate-Buffered Saline (PBS) (Invitrogen cat #14190). hHSC were deprived for 24 hours in serum-free and SteCGS-free medium.

For the treatments with NTZ, Elafibranor or other PPAR agonists and the respective NTZ/Elafibranor or PPAR agonists combinations, the serum-deprived hHSC were preincubated for 1 hour with the compounds followed by addition of the profibrogenic stimuli TGF-β1 (PeproTech cat #100-21, 1 ng/mL) in serum-free and SteCGS-free medium for an additional 48 hour period.

α-SMA ELISA

The level of α-SMA was measured using a Sandwich ELISA. Briefly, the wells of an ELISA plate were first coated with the capture antibody (mouse monoclonal anti-ACTA2, Abnova) at 4° C. overnight. After 3 washes in PBS+0.2% Tween 20, a blocking solution consisting of PBS+0.2% BSA was added for one hour followed by another washing cycle. The cell lysates were transferred into the wells for binding to the capture antibody for a period of 2 h at room temperature. After the washing procedure, the detection antibody (biotinylated mouse monoclonal anti-ACTA2, Abnova) was added for 2 hours at room temperature followed by 3 washes. For the detection, an HRP-conjugated Streptavidin (R&D Systems cat #DY998) was first applied for 30 min at room temperature. After washing, the HRP substrate TMB (BD, #555214) was added and incubated for 7 min at room temperature in the dark. Upon oxidation, TMB forms a water-soluble blue reaction product that becomes yellow with addition of sulfuric acid (solution stop), enabling accurate measurement of the intensity at 450 nm using a spectrophotometer. The developed color is directly proportional to the amount of α-SMA present in the lysate.

Determination of Synergism by Excess Over Bliss (EOB) Method and Confirmation by EOSHA (Excess Over Highest Single Agent)

The values obtained in the αSMA ELISA assays were first transformed into percentage inhibitions over TGF-β1 control. Then, using these percentage inhibitions, EOB (Excess Over Bliss) was determined to define the synergistic effects of drug combinations. Expected Bliss additivism score (E) was firstly determined by the equation:

$$E=(A+B)-(A\times B)$$

where A and B are the percentage inhibition of NTZ (A) and Elafibranor, Saroglitazar, Seladelpar, or Lanifibranor (B) at a given dose. The difference between the Bliss expectation and the observed inhibition of the combined NTZ/Elafibranor, Saroglitazar, Seladelpar, or Lanifibranor at the same dose is the 'Excess over Bliss' score.

Excess over Bliss score=0 indicates that the combination treatment is additive (as expected for independent pathway effects);

Excess over Bliss score >0 indicates activity greater than additive (synergy); and Excess over Bliss score <0 indicates the combination is less than additive (antagonism).

For the combination NTZ+Elafibranor, an additional total Bliss score was calculated by summation of all EOB.

EOHSA is a standard measure of synergy used by the FDA for evaluation of drug combinations and is calculated as the difference of the effect produced by the drug combination and the greatest effect produced by each of the combination's single agents at the same concentrations as when combined (Borisy et al., 2003). For synergistic combinations identified by the EOB method, the experimental % inhibition were plotted in a bar graph and the significance of the observed differences between NTZ/ELA and single agent were estimated by one-way ANOVA and uncorrected Fisher's LSD post-hoc (*: p<0.05; : p<0.01; *: p<0.001).

Evaluation of Elafibranor, Nitazoxanide and the Combination Elafibranor+Nitazoxanide in a Chronic CDAA+1% Cholesterol Model if Fibrosing NASH (12 Weeks)

Experimental Design

The choline-deficient and L-amino acid-defined (CDAA) diet lacks choline, which is essential for hepatic β-oxidation and very low density lipoprotein production, and is believed to induce hepatocytes to store fat and subsequently cause cellular damage. The CDAA diet-induced rodent model develops fibrosis within a relatively short period of time, ideal for rapidly studying the reversibility of NASH pathology, particularly fibrosis.

Increased cholesterol intake accelerates liver fibrosis in several mouse models of NASH. The exacerbation of liver fibrosis mainly involves free cholesterol accumulation in hepatic stellate cells, that sensitizes the cells to transforming growth factor β(TGFβ) and subsequently aggravates liver fibrosis.

In the current study, we examined the effects of nitazoxanide on liver fibrosis in C57Bl/6J mice fed a CDAA diet supplemented with 1% cholesterol.

The preventive effects of Elafibranor alone, NTZ alone and the combination of both were assessed in a fibrosing NASH-model of mice fed a CDAA+1% cholesterol diet. 6 week-old male C57Bl/6J mice were fed a control (CSAA) diet, CDAA+1% cholesterol diet, or CDAA+1% cholesterol diet supplemented with Elafibranor 1, and 3 mg/kg/day, NTZ 30 and 100 mg/kg/day or combined drugs (Elafibranor 1 and 3 mg/kg/day combined to NTZ 30 and 100 mg/kg/day) for 12 weeks.

The body weight and the food intake were monitored twice per week. On the last day of treatment, mice were sacrificed after a 6h fasting period. The liver was rapidly excised for biochemical and histological studies.

All animal procedures were performed according to standard protocols and in accordance with the standard recommendations for the proper care and use of laboratory animals. 6 weeks-old C57BL/6 male mice were fed for 12 weeks according to an experimental plan detailed in the table 1:

TABLE 1

| Experimental plan | | | |
|---|---|---|---|
| Diet | Compound | Dose mg/kg/day | Number of mice |
| CSAA | | | 8 |
| CDAA + 1% Chol | | | 12 |
| | Elafibranor | 1 | 8 |
| | | 3 | 8 |
| | NTZ | 30 | 8 |
| | | 100 | 8 |
| | Elafibranor + NTZ | 1 + 30 | 8 |
| | | 1 + 100 | 8 |
| | | 3 + 30 | 8 |
| | | 3 + 100 | 8 |

The control was the CSAA diet.

Some mice were fed with the CDAAc diet.

Some mice were fed with CDAAc diet supplemented with Elafibranor at 1 or 3 mg/kg/day.

Some mice were fed with CDAAc diet supplemented with NTZ at 30 or 100 mg/kg/day.

Some mice were fed with CDAAc diet supplemented with Elafibranor+NTZ combination at different ratios: 1+30, 1+100, 3+30 and 3+100 mg/kg/day.

The group corresponding to CDAAc diet supplemented with NTZ at 30 mg/kg is also named C57Bl/6J mice fed CDAA diet+nitazoxanide 0.02% (wt/wt) corresponding to the theoretical dose of 30 mg/kg/day.

The group corresponding to CDAAc diet supplemented with NTZ at 100 mg/kg is also named C57Bl/6J mice fed CDAA diet+nitazoxanide 0.0667% (wt/wt) corresponding to the theoretical dose of 100 mg/kg/day.

The food was purchased from Ssniff® company (Soest, Germany).

Nitazoxanide (cf reference in Table 1) was incorporated by Ssniff® into CDAA+1% chol diet in powder form to the required dose.

The reference and batch number of nitazoxanide are summarized in the table Table 2:

TABLE 2

| Nitazoxanide references | | | | |
|---|---|---|---|---|
| Compound | Laboratory code | | | |
| (INN) | External ID | Genfit ID | Supplier | Reference Batch |
| Nitazoxanide | GFE 50455 | GSL022597.08 | Interchim | RQ550 1501 |

For each dose a calculation of the exact doses was done according to the following example. This allows taking in count the exact dose of each product that was exactly consumed by each group of mice.

Calculation of the Actual Treatment Doses: Example with Nitazoxanide 0.02% (wt/wt)

Food intake is expressed in grams of food/grams of animal/day 0.02% of nitazoxanide in diet
  0.02 g of cpd/100 g of food=0.2 mg of cpd/g of food
Actual dose of cpd:
  0.2 mg of cpd/gram of food/gram of animal/day
    (0.2 mg of cpd/gram of food/gram of animal/day)×
      1000=(0.2 mg of cpd/gram of food/kg of animal/
      day)=200 mg of cpd/gram of food/kg of animal per
      day Consequently, multiplying by 200 the food intake value expressed in grams of food/grams of animal/day; the obtained value corresponds to the actual administered dose expressed in mg of NTZ/kg of animal/day.

In the same manner:
  For the dose of NTZ 0.00667% wt/wt, the actual treatment dose was obtained by multiplying the food intake value (grams of food/grams of animal/day) by 66.7.
  For the dose of NTZ 0.0667% wt/wt, the actual treatment dose was obtained by multiplying the food intake value (grams of food/grams of animal/day) by 667. According to the calculation the calculated dose versus estimated dose are given in the following tables 3 and 4.

TABLE 3 estimated and calculated doses for each compound a different doses

| Groups | GFT505 | | | NTZ |
|---|---|---|---|---|
| Estimated doses | 1 mpk | 3 mpk | 30 mpk | 100 mpk |
| Calculated doses | 1 mpk | 2.8 mpk | 26.3 mpk | 78.1 mpk |

TABLE 4 estimated and calculated doses for each combinations at different doses

| | Groups | | | | | | | |
|---|---|---|---|---|---|---|---|---|
| | Combo 1 | | Combo 2 | | Combo 3 | | Combo 4 | |
| | GFT505 | NTZ | GFT505 | NTZ | GFT505 | NTZ | GFT505 | NTZ |
| Estimated doses | 1 mpk | 30 mpk | 1 mpk | 100 mpk | 3 mpk | 30 mpk | 3 mpk | 100 mpk |
| Calculated doses | 0.9 mpk | 26.4 mpk | 0.9 mpk | 79.4 mpk | 2.9 mpk | 27.4 mpk | 2.8 mpk | 77.7 mpk |

The body weight and food intake were recorded twice a week throughout the study.

At the end of the treatment period, animals were anesthetized with isoflurane and blood samples were taken as described below. Animals were then sacrificed by cervical dislocation and beheaded for brain excision and weighing. The liver was also collected and weighed. Part of the liver was fixed in 4% formalin, embedded in paraffin and used for histological analyses. The remaining liver was snap frozen in liquid nitrogen and kept at −80° C. until use for further analyses.

Blood sampling was performed at sacrifice following a 6-hour fasting period. Blood samples were withdrawn under anesthesia by retro orbital puncture. Heparin tubes containing blood were rapidly centrifuged (15 minutes at 4,000 rpm/4° C.) and the plasma fraction was collected. Plasma aliquots were stored at −20° C. until further analyses.

Plasma Biochemistry
Alanine Amino Transferase (ALT)
The plasmatic concentration of ALT was determined using the appropriate Randox kit for Daytona automate (Randox, cat #AL 3801). Briefly, the ALT within the plasma sample enzymatically transforms α-oxoglutarate and L-alanine into L-glutamate and pyruvate. In the presence of NADH, the generated pyruvate is converted by lactate dehydrogenase to form L-lactate and NAD+. The kinetics of the reaction is studied and allows the plasmatic level of ALT to be calculated. Results are expressed in U/L.

Aspartate Amino Transferase (AST)
The plasmatic concentration of AST was determined using the appropriate Randox kit for Daytona automate (Randox, cat #AS 3804). Briefly, the AST within the plasma sample enzymatically transforms α-oxoglutarate and L-aspartate into L-glutamate and oxaloacetate. In the presence of NADH, the generated oxaloacetate is converted by malate dehydrogenase to form L-malate and NAD+. The kinetics of the reaction is studied and allows the plasmatic levels of AST to be calculated. Results are expressed in U/L.

Histology
At sacrifice, liver samples were processed for histological analysis and examined as follows.

Tissue Embedding and Sectioning
The liver slices were first fixed for 12 hours in formalin 4% solution. Then, the liver pieces were washed 30 minutes in PBS, and dehydrated in ethanol solutions (successive baths at 70, 80, 95 and 100% ethanol). The liver pieces were incubated in three different baths of Xylene (Sigma-Aldrich cat #534056), followed by two baths in liquid paraffin (60° C.). Liver pieces were then put into racks that were gently filled with Histowax® to completely cover the tissue.

The paraffin blocks containing the tissue pieces were removed from the racks and stored at room temperature. The liver blocks were cut into 3 μm slices.

Picrosirius Red Staining
Liver sections were deparaffinized, rehydrated and incubated for 15 minutes in a solution of Fast Green FCF 0.04% (Sigma-Aldrich, cat #F7258) before rinsing in a bath of 0.5% acetic acid (Sigma-Aldrich, cat #695092). Then, the liver sections were rinsed in water and incubated 30 minutes in a solution of Fast Green FCF 0.04%-0.1% sirius red (Direct Red 80, Fluka cat #43665) in saturated aqueous picric acid (Sigma-Aldrich cat #P6744). Sections were then dehydrated, and mounted using the CV Mount medium (Leica, cat #14046430011).

Histological Examinations
A technician blinded to the source of each liver specimen performed histological examinations. Virtual slides were generated using the Pannoramic 250 scanner from 3D Histech. Using Quant Center software (3D Histech, including Pattern Quant and Histo Quant modules), collagen-stained areas were quantified. Briefly, Pattern Quant was used to detect the tissue and measure its surface. Then, Histo Quant was used to detect the stained collagen content and measure its surface, based on a color threshold method. The fibrosis area was then expressed as the percentage of the collagen surface to the whole tissue for each animal.

Hepatic fibrosis staging was blind-evaluated, using CRN fibrosis criteria.

Details on the parameters, quantification/counting, and number of fields considered are provided in the following table 5.

TABLE 5

CRN's criteria for fibrosis

| Parameter | Points in score | Description (the entire section was considered) |
|---|---|---|
| Fibrosis | 0 | No fibrosis |
| | 1 | Centrilobular perisinusoidal/pericellular fibrosis or portal/periportal fibrosis |
| | 2 | Centrilobular perisinusoidal/pericellular fibrosis and portal/periportal fibrosis |
| | 3 | Centrilobular perisinusoidal/pericellular fibrosis and/or portal fibrosis with focal or extensive bridging fibrosis |
| | 4 | Cirrhosis |

Statistical Analysis

Experimental results were expressed as mean±standard deviation (SD) and plotted as bar graphs or curves. Statistical analyses were performed using Prism Version 7, as follows:

For the measures performed after sacrifice, CSAA vs CDAA+1% chol groups were compared by a Student t-test (#: $p<0.05$; ##: $p<0.01$; ###: $p<0.001$) or by a Mann-Whitney test (\$: $p<0.05$; \$\$: $p<0.01$; \$\$\$: $p<0.001$). Treatment groups were compared to CDAA+1% chol diet by one-way ANOVA and uncorrected Fisher's LSD post-hoc (*: $p<0.05$; : $p<0.01$; *: $p<0.001$).

Measurement of Hepatic Collagen Content

The hepatic collagen content was determined using the appropriate QuickZyme kit (Total collagen assay, cat #QZB-totcol5). The assay is based on the detection of hydroxyproline, which is a non-proteinogenic amino acid mainly found in the triple helix of collagen. Thus, hydroxyproline in tissue hydrolysates can be used as a direct measure of the amount of collagen present in the tissue (without discrimination between procollagen, mature collagen and collagen degradation products).

Complete hydrolysis of tissue samples in 6M HCl at 95° C. is required before dosing the hydroxyproline. The assay results in the generation of a chromogen with a maximum absorbance at 570 nm. Results are expressed as mg of collagen/g of liver.

Procollagen III N-Terminal Propeptide (PIIINP)

The plasmatic concentration of PIIINP was determined using an ELISA assay from Cloud-Clone Corp (cat #SEA573Ra), according to the manufacturer's instructions. The microtiter plate is pre-coated with an antibody specific to PIIINP. Standards or samples are added to the appropriate microtiter plate wells with a biotin-conjugated antibody specific to PIIINP. Next, Avidin conjugated to Horseradish Peroxidase (HRP) is added to each microplate well and incubated. After TMB substrate solution is added, only those wells that contain PIIINP, biotin-conjugated antibody and enzyme-conjugated Avidin will exhibit a change in color. The enzyme-substrate reaction is terminated by the addition of sulphuric acid solution and the color change is measured spectrophotometrically at a wavelength of 450 nm±10 nm. The concentration of PIIINP in the samples is then determined by comparing the OD of the samples to the standard curve. Results are expressed in pg/mL.

Gene Expression

RNA Extraction

Hepatic Total RNA was isolated using Nucleospin® 96 Kit (Macherey Nagel) following manufacturer's instructions. 150 ng of total RNA were reverse transcribed in cDNA using M-MLV-RT (Moloney Murine Leukemia Virus Reverse Transcriptase) (Invitrogen cat #28025) in presence of RT buffer 1× (Invitrogen cat #P/NY02321), 1 mM DTT (Invitrogen cat #P/NY00147), 0.5 mM dNTPs (Promega), 200 ng pdN6 (Roche cat #11034731001) and 40 U of Ribonuclease inhibitor (Promega cat #N2515).

Quantitative PCR was then carried out using the CFX96 Touch™ Real-Time PCR Detection System (Biorad). Briefly, PCR reactions were performed in 96 well plates on 5 μl of 5× diluted reverse transcription mix using the iQ SYBR Green Supermix kit (Biorad cat #170887). The experimental conditions were: 20 μL of volume reaction and 0.5 μL each of reverse and forward primers (10 pMol).

| Primer name | Sequence ID | Sequence (5'→3') |
|---|---|---|
| αSMA forward | 1 | CTGACAGAGGCACCACTGAA |
| αSMA reverse | 2 | CATCTCCAGAGTCCAGCACA |
| Col1α1 forward | 3 | AGGCGAACAAGGTGACAGAG |
| Col1α1 reverse | 4 | GCCAGGAGAACCAGCAGAG |
| Col1α2 forward | 5 | ATTGGAAGCCGAGGTCCCAG |
| Col1α2 reverse | 6 | TTTGCCCCCAGGTATGCCAG |
| TGFβ1 forward | 7 | TTGCTTCAGCTCCACAGAGA |
| TGFβ1 reverse | 8 | TGGTTGTAGAGGGCAAGGAC |
| TIMP1 forward | 9 | ATTCAAGGCTGTGGGAAATG |
| TIMP1 reverse | 10 | CTCAGAGTACGCCAGGGAAC |
| TIMP2 forward | 11 | GCATCACCCAGAAGAAGAGC |
| TIMP2 reverse | 12 | GGGTCCTCGATGTCAAGAAA |
| MMP2 forward | 13 | TCCCTAAGCTCATCGCAGAC |
| MMP2 reverse | 14 | GCTTCCAAACTTCACGCTCT |
| MMP7 forward | 15 | TAATTGGCTTCGCAAGGAGA |
| MMP7 reverse | 16 | AAGGCATGACCTAGAGTGTTCC |
| CCR2 forward | 17 | TAATATGTTACCTCAGTTCATCCACGG |
| CCR2 reverse | 18 | TGCTCTTCAGCTTTTTACAGCCTATC |
| CCR5 forward | 19 | ATTCTCCACACCCTGTTTCG |
| CCR5 reverse | 20 | GAATTCCTGGAAGGTGGTCA |
| GAPDH forward | 21 | TATGACTCCACTCACGGCAA |
| GAPDH reverse | 22 | TCCACGACATACTCAGCACC |

Expression levels were normalized using the expression of GAPDH gene as reference.

For each gene, the standard curve was drawn by selecting the best points (at least three points) in order to have PCR reaction efficiency close to 100% and a correlation coefficient close to 1. Expression levels were determined using the standard curve equation for both the housekeeping gene and the target gene (taking into account the specific PCR efficiency of each target gene).

RESULTS AND CONCLUSIONS

The abnormal persistence of differentiated myofibroblasts is a characteristic of many fibrotic diseases.

Following liver injury, quiescent HSCs undergo a process of activation that is characterized by a differentiation into ($\alpha$-SMA)-positive myofibroblasts.

NTZ as a single agent was shown to confer an anti-fibrotic activity in TGF$\beta$-induced hHSC (FIG. 1B). Since it is known that NTZ is rapidly hydrolyzed into its active metabolite tizoxanide (TZ) (Broekhuysen, Stockis et al., 2000), this metabolite was also evaluated for its antifibrotic activity in HSC. TZ showed a profile similar to the parent drug (data not shown). On the other hand, some PPAR agonists like Elafibranor also revealed an antifibrotic profile in the TGF$\beta$ induced HSC model (FIG. 1A). Other PPAR agonists like bezafibrate revealed a weak activity suggesting that PPAR agonists are not equivalent regarding their antifibrotic properties (FIG. 1C).

In order to evaluate if a combination of Elafibranor with NTZ could reduce fibrosis in a synergistic manner, combination matrix experiments were performed in TGF$\beta$-induced HSCs. Briefly, NTZ and Elafibranor solutions were serially diluted in a checkerboard format generating a 42 combinations matrix covering a large panel of Elafibranor/NTZ ratios. Synergy was first determined by calculating Excess Over Bliss scores. These experiments revealed that NTZ could synergize with Elafibranor to reduce $\alpha$-SMA production in activated HSCs. Several combination pairs revealed an EOB score over 10, which is indicative of a synergism (FIG. 2B).

To validate the synergism, the experimental values corresponding to top EOB score were plotted in a bar graph (FIG. 2C). These graphs illustrate that the combination of NTZ with Elafibranor shows a superior antifibrotic effect that is statistically significant compared to the highest single agent (NTZ or Elafibranor). The most impressive example is represented with the combination pair NTZ at 0.6 µM and Elafibranor at 5 µM. Although NTZ shows almost no antifibrotic activity at 0.6 µM, the addition of Elafibranor at 5 µM results in a strong reduction of $\alpha$SMA of 55%, which is much stronger than the effect observed with the single agents alone. In order to evaluate if a combination of other PPAR agonists, Sarogliatzar, Seladelpar and Lanifibranor with NTZ, could reduce fibrosis in a synergistic manner, combination matrix experiments were also performed in TGF$\beta$-induced HSCs and EOB score were determined. To assess the synergism with the combination of NTZ with Sarogliatazar, Seladelpar and Lanifibranor were validated on antifibrotic activity. The combination of NTZ with Sarogliatzar, Seladelpar, or Lanifibranor revealed an EOB score >0, which is indicative of a synergism. The combination of Sarogliatzar at 2.5 µM and NTZ at 0.625 µM results also in a strong reduction of $\alpha$SMA of 52%, which is much stronger than the effect observed with the single agents alone (FIG. 3A). The combination of Seladelpar at 20 µM and NTZ at 2.5 µM also results in a strong reduction of $\alpha$SMA of 72%, which is much stronger than the effect observed with the single agents alone (FIG. 3B). To a lesser extent, the combination of Lanifibranor at 10 µM and NTZ at 1.25 µM tends to be significant (p=0.06) to reduce $\alpha$-SMA production in activated HSCs compared to NTZ (FIG. 3C).

In conclusion, the applicant has discovered unexpected antifibrotic activities for a combination of a compound of Formula (I) with specific PPAR agonist(s). These results suggest that a combination of a compound of Formula (I) with a PPAR agonist can be synergistic and can provide therapeutic benefits in multiple types of fibrotic diseases.

The administration of a choline-deficient and L-amino acid-deficient (CDAA)+1% cholesterol diet to mice causes progressive fibrosing steatohepatitis that is pathologically similar to human non-alcoholic steatohepatitis (NASH).

The CDAA+1% cholesterol diet notably induces a significant increase in the hepatic collagen, as shown in the FIG. 4.

This figure also shows that administration of Elafibranor or NTZ alone decreases the hepatic collagen content. The decrease in collagen is proportional to the dose of elafibranor or NTZ administered.

When a combination of Elafibranor and NTZ is administered, the decrease in collagen produced is greater than the decrease observed for each compound taken separately.

There is therefore a synergistic effect of the combination of elafibranor and NTZ on the decrease in collagen production. In other words, there is a noticed anti-fibrotic effect when Elafibranor and NTZ are combined.

The better effect is observed for the combination comprising Elafibranor at 2.8 mpk (mg per kilogram) and NTZ at 77.7 mpK, expressed in calculated doses.

FIG. 5 represents the results obtained with the histology, i.e. the determination of the fibrosis area which was expressed as the percentage of the collagen surface to the whole tissue for each animal.

The CDAA+1% cholesterol diet notably induces a significant increase in the fibrosis percentage.

FIG. 5 also shows that administration of Elafibranor or NTZ alone decreases the fibrosis percentage. The decrease is proportional to the dose of elafibranor or NTZ administered.

When a combination of Elafibranor and NTZ is administered, the decrease in fibrosis percentage is greater than the decrease observed for each compound taken separately.

There is therefore a synergistic effect of the combination of elafibranor and NTZ on the decrease in the fibrosis percent. In other words, there is a noticed anti-fibrotic effect when Elafibranor and NTZ are combined.

The better effect is observed for the combination comprising Elafibranor at 2.8 mpk (mg per kilogram) and NTZ at 77.7 mpK, expressed in calculated doses.

FIGS. 6 to 12 represent the gene expression of different hepatic markers of fibrosis. For all markers, the CDAA+1% cholesterol diet notably induces a significant increase in the gene expressions.

It can also be noted that that administration of Elafibranor or NTZ alone decreases the level of the different gene expression. The decrease is proportional to the dose of elafibranor or NTZ administered.

When a combination of Elafibranor and NTZ is administered, the decrease in gene expression is greater than the decrease observed for each compound taken separately.

There is therefore a synergistic effect of the combination of elafibranor and NTZ on the decrease in the gene expression of different hepatic markers of fibrosis. In other words, there is a noticed synergistic anti-fibrotic effect when Elafibranor and NTZ are combined.

In conclusion, the applicant has discovered unexpected synergistic antifibrotic activities for a combination of a compound of Formula (I) with specific PPAR agonist(s).

These results suggest that a combination of a compound of Formula (I) with a PPAR agonist can be synergistic and/or can have additional effects and can also provide therapeutic benefits in multiple types of fibrotic diseases.

REFERENCES

Broekhuysen, J., A. Stockis, et al. (2000). "Nitazoxanide: pharmacokinetics and metabolism in man." Int J Clin Pharmacol Ther 38(8): 387-394.

Borisy, A. A., Elliott, P. J., Hurst, N. W., Lee, M. S., Lehar, J., Price, E. R., Serbedzija, G., Zimmermann, G. R., Foley, M. A., Stockwell, B. R., Keith C. T. Systematic discovery of multicomponent therapeutics. Proc Natl Acad Sci USA. 2003 Jun. 24; 100(13):7977-82.

de Carvalho, L. P. S., C. M. Darby, et al. (2011). "Nitazoxanide disrupts membrane potential and intrabacterial pH homeostasis of Mycobacterium tuberculosis." ACS Med. Chem. Lett. 2 (Copyright (C) 2015 American Chemical Society (ACS). All Rights Reserved.): 849-854.

Di Santo, N. and J. Ehrisman (2014). "A functional perspective of nitazoxanide as a potential anticancer drug." Mutat. Res., Fundam. Mol. Mech. Mutagen. 768 (Copyright (C) 2015 American Chemical Society (ACS). All Rights Reserved.): 16-21.

Dubreuil, L., I. Houcke, et al. (1996). "In vitro evaluation of activities of nitazoxanide and tizoxanide against anaerobes and aerobic organisms." Antimicrob. Agents Chemother. 40 (Copyright (C) 2015 American Chemical Society (ACS). All Rights Reserved.): 2266-2270.

Finegold, S. M., D. Molitoris, et al. (2009). "Study of the in vitro activities of rifaximin and comparator agents against 536 anaerobic intestinal bacteria from the perspective of potential utility in pathology involving bowel flora." Antimicrob. Agents Chemother. 53 (Copyright (C) 2015 American Chemical Society (ACS). All Rights Reserved.): 281-286.

Fox, L. M. and L. D. Saravolatz (2005). "Nitazoxanide: a new thiazolide antiparasitic agent." Clin. Infect. Dis. 40 (Copyright (C) 2015 American Chemical Society (ACS). All Rights Reserved.): 1173-1180.

Hemphill, A., J. Mueller, et al. (2006). "Nitazoxanide, a broad-spectrum thiazolide anti-infective agent for the treatment of gastrointestinal infections." Expert Opin. Pharmacother. 7 (Copyright (C) 2015 American Chemical Society (ACS). All Rights Reserved.): 953-964.

Hoffman, P. S., G. Sisson, et al. (2007). "Antiparasitic drug nitazoxanide inhibits the pyruvate oxidoreductases of Helicobacter pylori, selected anaerobic bacteria and parasites, and Campylobacter jejuni." Antimicrob. Agents Chemother. 51 (Copyright (C) 2015 American Chemical Society (ACS). All Rights Reserved.): 868-876.

Megraudd, F., A. Occhialini, et al. (1998). "Nitazoxanide, a potential drug for eradication of Helicobacter pylori with no cross-resistance to metronidazole." Antimicrob. Agents Chemother. 42 (Copyright (C) 2015 American Chemical Society (ACS). All Rights Reserved.): 2836-2840.

Pankuch, G. A. and P. C. Appelbaum (2006). "Activities of tizoxanide and nitazoxanide compared to those of five other thiazolides and three other agents against anaerobic species." Antimicrob. Agents Chemother. 50 (Copyright (C) 2015 American Chemical Society (ACS). All Rights Reserved.): 1112-1117.

Rossignol, J.-F. (2014). "Nitazoxanide: A first-in-class broad-spectrum antiviral agent." Antiviral Res. 110 (Copyright (C) 2015 American Chemical Society (ACS). All Rights Reserved.): 94-103.

Rossignol, J. F. and R. Cavier (1975). 2-Benzamido-5-nitrothiazoles, S.P.R.L. Phavic, Belg. 11 pp.

Rossignol, J. F. and H. Maisonneuve (1984). "Nitazoxanide in the treatment of Taenia saginata and Hymenolepis nana infections." Am J Trop Med Hyg 33 (Copyright (C) 2015 U.S. National Library of Medicine.): 511-512.

The invention claimed is:

1. A method for treating an inflammatory, metabolic, fibrotic or cholestatic disease modulated by transforming growth factor β (TGF-β) in a subject in need thereof, the method comprising administering to the subject:
   (i) a compound selected from the group consisting of nitazoxanide (NTZ), tizoxanide, and a pharmaceutically acceptable salt thereof; and
   (ii) at least one PPAR agonist selected from the group consisting of elafibranor, seladelpar, saroglitazar, lanifibranor, and a pharmaceutical salt thereof.

2. The method of claim 1, wherein the method comprises administering to the subject:
   (i) a compound selected from the group consisting of nitazoxanide, tizoxanide, and a pharmaceutical salt thereof; and
   (ii) Elafibranor or a pharmaceutically acceptable salt thereof.

3. The method of claim 1, wherein the compound and the at least one PPAR agonist is in a composition further comprising a pharmaceutically acceptable carrier.

4. The method of claim 1, wherein the compound and the at least one PPAR agonist is in a kit for sequential, separate or simultaneous use.

5. The method of claim 1, wherein the compound and the at least one PPAR agonist are formulated in an injectable suspension, a gel, an oil, a pill, a tablet, a suppository, a powder, a capsule, an aerosol, an ointment, a cream, a patch, or means of galenic forms for a prolonged and/or slow release.

6. The method of claim 1, wherein the fibrotic disease is selected from the group consisting of liver, kidney, skin, epidermis, endodermis, muscle, tendon, cartilage, heart, pancreas, lung, uterus, nervous system, testis, ovary, adrenal gland, artery, vein, colon, intestine, biliary tract, soft tissue, bone marrow, joint and stomach fibrosis.

7. The method of claim 1, wherein the inflammatory, metabolic, fibrotic or cholestatic disease is selected from the group consisting of, metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies.

8. The method of claim 1, wherein the fibrotic disease is selected from the group consisting of liver, gut, lung, heart, kidney, muscle, skin, soft tissue, bone marrow, intestinal, and joint fibrosis.

9. The method of claim 1, wherein the inflammatory, metabolic, fibrotic or cholestatic disease is primary sclerosing cholangitis (PSC), or primary biliary cholangitis (PBC).

* * * * *

SEQUENCE LISTING

```
<160> NUMBER OF SEQ ID NOS: 22

<210> SEQ ID NO 1
<211> LENGTH: 20
<212> TYPE: DNA
<213> ORGANISM: artificial
<220> FEATURE:
<223> OTHER INFORMATION: alpha-SMA forward

<400> SEQUENCE: 1
ctgacagagg caccactgaa                                                  20

<210> SEQ ID NO 2
<211> LENGTH: 20
<212> TYPE: DNA
<213> ORGANISM: artificial
<220> FEATURE:
<223> OTHER INFORMATION: alpha-SMA reverse

<400> SEQUENCE: 2
catctccaga gtccagcaca                                                  20

<210> SEQ ID NO 3
<211> LENGTH: 20
<212> TYPE: DNA
<213> ORGANISM: artificial
<220> FEATURE:
```

```
<223> OTHER INFORMATION: Col1a1 forward

<400> SEQUENCE: 3
aggcgaacaa ggtgacagag                                           20

<210> SEQ ID NO 4
<211> LENGTH: 19
<212> TYPE: DNA
<213> ORGANISM: artificial
<220> FEATURE:
<223> OTHER INFORMATION: Col1a1 reverse

<400> SEQUENCE: 4
gccaggagaa ccagcagag                                            19

<210> SEQ ID NO 5
<211> LENGTH: 20
<212> TYPE: DNA
<213> ORGANISM: artificial
<220> FEATURE:
<223> OTHER INFORMATION: Col1a2 forward

<400> SEQUENCE: 5
attggaagcc gaggtcccag                                           20

<210> SEQ ID NO 6
<211> LENGTH: 20
<212> TYPE: DNA
<213> ORGANISM: artificial
<220> FEATURE:
<223> OTHER INFORMATION: Col1a2 reverse

<400> SEQUENCE: 6
tttgccccca ggtatgccag                                           20

<210> SEQ ID NO 7
<211> LENGTH: 20
<212> TYPE: DNA
<213> ORGANISM: artificial
<220> FEATURE:
<223> OTHER INFORMATION: TGFb1 forward

<400> SEQUENCE: 7
ttgcttcagc tccacagaga                                           20

<210> SEQ ID NO 8
<211> LENGTH: 20
<212> TYPE: DNA
<213> ORGANISM: artificial
<220> FEATURE:
<223> OTHER INFORMATION: TGFb1 reverse

<400> SEQUENCE: 8
tggttgtaga gggcaaggac                                           20

<210> SEQ ID NO 9
<211> LENGTH: 20
<212> TYPE: DNA
<213> ORGANISM: artificial
<220> FEATURE:
<223> OTHER INFORMATION: TIMP1 forward

<400> SEQUENCE: 9
attcaaggct gtgggaaatg                                           20
```

```
<210> SEQ ID NO 10
<211> LENGTH: 20
<212> TYPE: DNA
<213> ORGANISM: artificial
<220> FEATURE:
<223> OTHER INFORMATION: TIMP1 reverse

<400> SEQUENCE: 10
ctcagagtac gccagggaac                                               20

<210> SEQ ID NO 11
<211> LENGTH: 20
<212> TYPE: DNA
<213> ORGANISM: artificial
<220> FEATURE:
<223> OTHER INFORMATION: TIMP2 forward

<400> SEQUENCE: 11
gcatcaccca gaagaagagc                                               20

<210> SEQ ID NO 12
<211> LENGTH: 20
<212> TYPE: DNA
<213> ORGANISM: artificial
<220> FEATURE:
<223> OTHER INFORMATION: TIMP2 reverse

<400> SEQUENCE: 12
gggtcctcga tgtcaagaaa                                               20

<210> SEQ ID NO 13
<211> LENGTH: 20
<212> TYPE: DNA
<213> ORGANISM: artificial
<220> FEATURE:
<223> OTHER INFORMATION: MMP2 forward

<400> SEQUENCE: 13
tccctaagct catcgcagac                                               20

<210> SEQ ID NO 14
<211> LENGTH: 20
<212> TYPE: DNA
<213> ORGANISM: artificial
<220> FEATURE:
<223> OTHER INFORMATION: MMP2 reverse

<400> SEQUENCE: 14
gcttccaaac ttcacgctct                                               20

<210> SEQ ID NO 15
<211> LENGTH: 20
<212> TYPE: DNA
<213> ORGANISM: artificial
<220> FEATURE:
<223> OTHER INFORMATION: MMP7 forward

<400> SEQUENCE: 15
taattggctt cgcaaggaga                                               20

<210> SEQ ID NO 16
<211> LENGTH: 22
<212> TYPE: DNA
<213> ORGANISM: artificial
<220> FEATURE:
<223> OTHER INFORMATION: MMP7 reverse
```

```
<400> SEQUENCE: 16
aaggcatgac ctagagtgtt cc                                            22

<210> SEQ ID NO 17
<211> LENGTH: 27
<212> TYPE: DNA
<213> ORGANISM: artificial
<220> FEATURE:
<223> OTHER INFORMATION: CCR2 forward

<400> SEQUENCE: 17
taatatgtta cctcagttca tccacgg                                       27

<210> SEQ ID NO 18
<211> LENGTH: 26
<212> TYPE: DNA
<213> ORGANISM: artificial
<220> FEATURE:
<223> OTHER INFORMATION: CCR2 reverse

<400> SEQUENCE: 18
tgctcttcag cttttacag cctatc                                         26

<210> SEQ ID NO 19
<211> LENGTH: 20
<212> TYPE: DNA
<213> ORGANISM: artificial
<220> FEATURE:
<223> OTHER INFORMATION: CCR5 forward

<400> SEQUENCE: 19
attctccaca ccctgtttcg                                               20

<210> SEQ ID NO 20
<211> LENGTH: 20
<212> TYPE: DNA
<213> ORGANISM: artificial
<220> FEATURE:
<223> OTHER INFORMATION: CCR5 reverse

<400> SEQUENCE: 20
gaattcctgg aaggtggtca                                               20

<210> SEQ ID NO 21
<211> LENGTH: 20
<212> TYPE: DNA
<213> ORGANISM: artificial
<220> FEATURE:
<223> OTHER INFORMATION: GAPDH forward

<400> SEQUENCE: 21
tatgactcca ctcacggcaa                                               20

<210> SEQ ID NO 22
<211> LENGTH: 20
<212> TYPE: DNA
<213> ORGANISM: artificial
<220> FEATURE:
<223> OTHER INFORMATION: GAPDH reverse

<400> SEQUENCE: 22
tccacgacat actcagcacc                                               20
```